US010004768B2

(12) United States Patent
Kubo

(10) Patent No.: US 10,004,768 B2
(45) Date of Patent: Jun. 26, 2018

(54) TREATMENT OF ATOPIC DERMATITIS AND INFECTIOUS DERMATITIS WITH BIOLOGICAL SPA THERAPY

(71) Applicant: Iryohojin Kiyokai, Takayama-shi, Gifu (JP)

(72) Inventor: Kensuke Kubo, Takayama (JP)

(73) Assignee: Iryohojin Kiyokai, Takayama-shi (JP)

(*) Notice: Subject to any disclaimer, the term of this patent is extended or adjusted under 35 U.S.C. 154(b) by 353 days.

(21) Appl. No.: 14/496,398

(22) Filed: Sep. 25, 2014

(65) Prior Publication Data

US 2016/0089403 A1    Mar. 31, 2016

(51) Int. Cl.
*A61K 35/74* (2015.01)
*A61K 35/742* (2015.01)
*A61K 9/00* (2006.01)

(52) U.S. Cl.
CPC .......... *A61K 35/742* (2013.01); *A61K 9/0014* (2013.01); *A61K 9/0095* (2013.01)

(58) Field of Classification Search
CPC .................................................. A61K 35/742
See application file for complete search history.

(56) References Cited

U.S. PATENT DOCUMENTS

| 6,723,326 B1* | 4/2004 | Farmer | A01N 63/00 424/246.1 |
| 7,807,185 B2* | 10/2010 | Farmer | A01N 63/00 424/184.1 |
| 2003/0003107 A1* | 1/2003 | Farmer | A01N 63/00 424/184.1 |
| 2009/0186057 A1 | 7/2009 | Farmer et al. | |
| 2011/0274676 A1 | 11/2011 | Farmer et al. | |

FOREIGN PATENT DOCUMENTS

| JP | H04-297211 A | 10/1992 |
| JP | H08-131158 | 5/1996 |
| JP | 2002-512615 | 4/2002 |
| JP | 2005-230041 A | 9/2005 |
| JP | 2006-102304 A | 4/2006 |
| JP | 2008-045793 A | 2/2008 |
| JP | 2008-149307 A | 7/2008 |

OTHER PUBLICATIONS

Cawoy, H., et al., "Bacillus-Based Biological Control of Plant Diseases," in Pesticides in the Modern World—Pesticides Use and Management, Stoytcheva, M. (Ed.), InTech: Rijeka, Croatia (2011), pp. 273-302.
Deckers, I.A.G., et al., "Investigating International Trends in the Incidence and Prevalence of Atopic Eczema 1990-2010: A Systemic Review of Epidemioliogical Studies," PLoS ONE, vol. 7, Issue 7, e39803 (pp. 1-28) (2012).
Kitamura, T., et al., "Effect of Water Temperature on the Survival of *Cryptosporidium parvum* Oocytsts by in Vitro Excystation-Flow Cytometry Assay," Enviornmental Engineering Research, vol. 37, pp. 355-360 (2000). [abstract].
Van Rensburg, C.E.J., et al., "An in Vitro Investigation of the Antimicrobial Activity of Oxifulvic Acid," J. Antimicrob, Chemother., vol. 46, pp. 853-854 (2000).
Notification of Reasons for Refusal corresponding to Japanese Application No. 2013-190646 dated Jul. 25, 2017.
Eichenfield et al. (2014a) Guidelines of care for the management of atopic dermatitis. Section 1 Diagnosis and assessment of atopic dermatitis. Am Acad Dermatol 70(2):338-351.
Eichenfield et al. (2014b) Guidelines of care for the management of atopic dermatitis. Section 2. Management and treatment of atopic dermatitis with topical therapies. J Am Acad Dermatol 71(1):116-132.
Kakinuma et al. (Mar. 2001) Thymus and activation-regulated chemokine in atopic dermatitis: Serum thymus and activation-regulated chemokine level is closely related with disease activityJ Allergy Clin Immunol 107(3):535-541.
Sidbury et al. (2014a) Guidelines of care for the management of atopic dermatitis Section 3. Managment and treatment with phototherapy and systemic agents. J Am Acad Dermatol. 71(2):327-349.
Sidbury et al. (2014b) Guidelines of care for the management of atopic dermatitis. Section 4. Prevention of disease flares and use of adjunctive therapies and approaches. J Am Acad Dermatol 1-16.
Beck et al. (2014a) Dupilumab Treatment in Adults with Moderate-to-Severe Atopic Dermatitis. N Engl J Med 371(2):130-139.
Beck et al. (2014b) Supplementary Appendix—Dupilumab Treatment in Adults with Moderate-to-Severe Atopic Dermatitis. N Engl J Med 371(2):130-139.
Darabi (2009) et al. The Role of Malassezia in Atopic Dermatitis Affecting the Head and Neck of Adults. J. Am. Acad. Dermatol. 60(1):125-136.
Etchegaray et al. (2008) Effect of a Highly Concentrated Lipopetide Extract of Bacillus subtilis on Fungal and Bacterial Cells. Arch. Microbiol. 190(6):611-622.
Gans et al. (2005) Computational Improvements Reveal Great Bacterial Diversity and High Metal Toxicity in Soil. Science 309(5739):1387-1390.
Gueho et al. (1996) The genus *Malassezia* with Description of Four New Species. Antonie van Leeuwenhoek 69(4):337-355.
Hijnen et al. (2004) Serum Thymus and Activation-Regulated Chemokine (TARC) and Cutaneous T Cell—Attracting Chemokine (CTACK) Levels in Allergic Disease: TARC and CTACK are Disease—Specific Markers for Atopic Dermatitis. J. Allergy Clin. Immunol. 113(2):334-340.
Hiraoka et al. (1992) Characteristics of Bacillus subtilis RB14, Coproducer of Peptide Antibiotics Iturin A and Surfactin. The Journal of General and Applied Microbiology 38:635-640 (1992).
Kaneko et al. (2007) Revised Culture-Based System for Identification of *Malassezia* Species. J. Clin. Microbial. 45(11):3737-3742.

(Continued)

*Primary Examiner* — Taeyoon Kim
*Assistant Examiner* — Tiffany M Gough
(74) *Attorney, Agent, or Firm* — Jenkins, Wilson, Taylor & Hunt, P.A.

(57) ABSTRACT

Provided is a method for treatment of atopic dermatitis and infectious dermatitis with biological spa therapy. The method seeks to cure or alleviate symptoms of atopic dermatitis by bathing in a bathwater containing, as dominant bacteria, not less than $10^5$ *Bacillus* bacteria per 1 mL of the bathwater.

14 Claims, 15 Drawing Sheets

(56) References Cited

OTHER PUBLICATIONS

Mahe et al. (2013) A new Vitreoscilla filiformis extract grown on spa water-enriched medium.activates endogenous cutaneous antioxidant and antimicrobial defenses through a potential Toll-like receptor 2/protein kinase C, zeta transduction pathway. Clinical, Cosmetic and Investigational Dermatology 2013:6:191-196.

Notification of Reasons for Refusal corresponding to Japanese Application No. 2013-190646 dated Jul. 20, 2017.

Schlievert et al. (2008) Superantigen Profile of *Staphylococcus aureus* Isolates From Patients with Steroid-Resistant Atopic Dermatitis. Clin. Infect. Dis. 46(10):1562-1567.

Schmitt et al. (2007) European Dermato-Epidemiology Network: What are the Best Outcome Measurements for Atopic Eczema? A Systemic Review. J. Allergy Clin. Immunol. 120:1389-1398.

Sugimoto et al. (2006) The Importance of Bacterial Superantigens Produced by *Staphylococcus aureus* in the Treatment of Atopic Dermatitis using Povidone-Iodine. Dermatology 212(Suppl. 1):26-34.

Sugita et al. (2006) Quantitative Analysis of Cutaneous Malassezia in Atopic Dermatitis Patients Using Real-Time PCT. Microbiology and Immunology 50(7):549-552.

Tamaki et al. (2006a) Serum TARC/CCL17 Levels as a Disease Marker of Atopic Dermatitis. Japanese Journal of Dermatology 116:27-39.

Tamaki et al. (2006b) Serum Levels of CCL17/TARC in Various Skin Diseases. J. Dermatol 33(4):300-302.

Volz et al. (2014) Non-pathogenic bacteria alleviating atopic dermatitis inflammation induce IL-10 producing dendritic cells and regulatory Tr1 cells. Journal of Investigative Dermatoloty 134(1);96-104.

Volz et al. (2014) Non-pathogenic bacteria alleviating atopic dermatitis inflammation induce IL-10 producing dendritic cells and regulatory Tr1 cells. pp. 1-7.

WHO (World Health Organization) (1996) Guidelines for Drinking Water Quality, Second Edition, vol. 2, Health Criteria and Other Supporting Information. pp. 1-22.

Williams et al. (2008) Is Eczema Really on the Increase Worldwide? ISAAC: International Study of Asthma and Allergies in Childhood. J. Allergy Clin. Immunol. 121(4):947-954.

\* cited by examiner

COURSE OF CASE A

COURSE OF CASE B

TREATMENT OF ATOPIC DERMATITIS AND INFECTIOUS DERMATITIS WITH BIOLOGICAL SPA THERAPY

BACKGROUND

The present invention relates to treatment of atopic dermatitis and infectious dermatitis with biological spa therapy.

As one of methods for treatment of dermatitis, some enthusiasts used to conduct a folk remedy of bathing in the bathwater that contains fermentation powder of Makomo (see, for example, Japanese Unexamined Patent Application Publication No. H08-131158) suspended therein and that is not changed over a long period of time. However, such a folk remedy did not exhibit constant effects, and neither clarification of scientific mechanism nor water quality management was conducted. As a result, foul odor and/or exacerbation of dermatitis occurred frequently, and the folk remedy was not widely spread.

SUMMARY

Against the above-described background, the inventor of the present invention had given a great deal of consideration over the years about problems in the conventional bathing therapy and causes of the problems. Such consideration led the inventor to gain knowledge as below.

(1) Therapeutic effects against atopic dermatitis result not from the fermentation powder of Makomo itself but from certain species of bacteria that grow in the bathwater.

Further, one of components that stabilize the water quality and facilitate growth of useful bacteria is a humic substance such as fulvic acid.

(2) In the above-described folk remedy, types of dominant bacteria growing in the bathwater change with time. Thus, even if useful bacteria have grown to thereby produce therapeutic effects temporarily, other types of bacteria may become dominant bacteria with time, and the therapeutic effects may be reduced. Furthermore, in the worst case, such a bathwater environment could lead not only to reduction of the therapeutic effects but also to exacerbation of dermatitis.

(3) It was believed that some effectiveness was caused by not changing the bathwater over a long period of time. In addition, it was recommended that a large amount of fermentation powder of Makomo, for example 400 g or more per month, be added into the bathwater. These led, in some cases, to occurrence of foul odor from the bathwater due to anaerobic metabolism, and/or growth of harmful pathogenic bacteria due to not performing temperature management, which ended up with failure to keep the bathwater in a state suitable for bathing therapy.

In view of the above-described circumstances, it is preferable to provide a method for treatment of atopic dermatitis and infectious dermatitis with biological spa therapy, in which the problems in the folk remedy have been improved on the basis of the above-described knowledge.

A method for treatment of atopic dermatitis and infectious dermatitis with biological spa therapy to be described below is a method that seeks to cure or alleviate symptoms of atopic dermatitis by bathing in a bathwater containing, as dominant bacteria, not less than $10^5$ *Bacillus* bacteria per 1 mL of the bathwater.

The inventor has found that existence of *Bacillus* bacteria in the bathwater as dominant bacteria plays a significant role in cure or alleviation of symptoms of atopic dermatitis, and this treatment method has been completed based on such a finding.

As described above, addition of the fermentation powder of Makomo into the bathwater itself had been conducted in the known folk remedy, too. In the folk remedy, however, reasons for onset of the therapeutic effects remained unexplained. Moreover, it was believed that some effectiveness was caused by not changing the bathwater over a long period of time. Thus, in the known folk remedy, there were cases where dominant bacteria in the bathwater were unstable and the environment in which beneficial bacteria were growing could not be maintained appropriately.

In one example, there were many situations in which, even if *Bacillus* bacteria grew at an early stage, for example, *Pseudomonas* bacteria gradually became predominant in the long term. In such a case, *Bacillus* bacteria become nonexistent in the bathwater. As a result, if the bathing is performed using such bathwater, atopic dermatitis could not be controlled, and negative effects such as exacerbation of symptoms were caused in some cases.

To cope with this, in the method for treatment of atopic dermatitis and infectious dermatitis with biological spa therapy proposed herein, bathing is performed using a bathwater containing, as dominant bacteria, not less than $10^5$ *Bacillus* bacteria per 1 mL of the bathwater. *Bacillus* bacteria have very low pathogenicity, have strong inhibitory effect against pathogenic bacteria such as dermal fungus and *Staphylococcus aureus*, and have strong inhibitory effect against pathogenic bacteria in the bathwater. In addition, *Bacillus* bacteria decompose and metabolize waste products discharged from the human body, whereby inhibiting chemical substances harmful to dermatitis from occurring in the bathwater.

Moreover, *Bacillus* bacteria can inhibit pathogenic bacteria such as yeast and fungus in the bathwater, whereby enabling maintenance of water quality suitable for the treatment. Therefore, cure or alleviation of symptoms of atopic dermatitis can be sought by bathing in the bathwater in which such *Bacillus* bacteria are growing.

In order to ensure such actions and effects, it is important for the bathwater to contain not less than $10^5$ *Bacillus* bacteria per 1 mL of the bathwater. It is preferable for the bathwater to contain about $10^5$-$10^8$ *Bacillus* bacteria per 1 mL of the bathwater.

This therapy has effects not only on treatment of atopic dermatitis in humans but also on infectious dermatitis caused by infection with pathogenic microorganisms, such as *Malassezia* and *Candida*, by virtue of inhibitory effect against infectious pathogens on the skin. Such infectious dermatitis includes, for example, *Malassezia* folliculitis, seborrheic dermatitis, *Candida* dermatitis, dermatitis caused by fungus such as ringworm, contagious impetigo (impetigo contagiosa) caused by infection with *Staphylococcus aureus*, etc., sudoriparous abscess, and folliculitis.

In addition, effects similar to those for humans are considered to be exerted on atopic dermatitis of pets, such as cats and dogs, caused by similar types of bacteria, and infectious dermatitis such as *Malassezia* folliculitis of pets, caused by pathogenic bacteria and fungi.

BRIEF DESCRIPTION OF THE DRAWINGS

The present invention will now be described by way of example with reference to the accompanying drawings, in which.

DETAILED DESCRIPTION OF THE PREFERRED EMBODIMENTS

Figure 1:
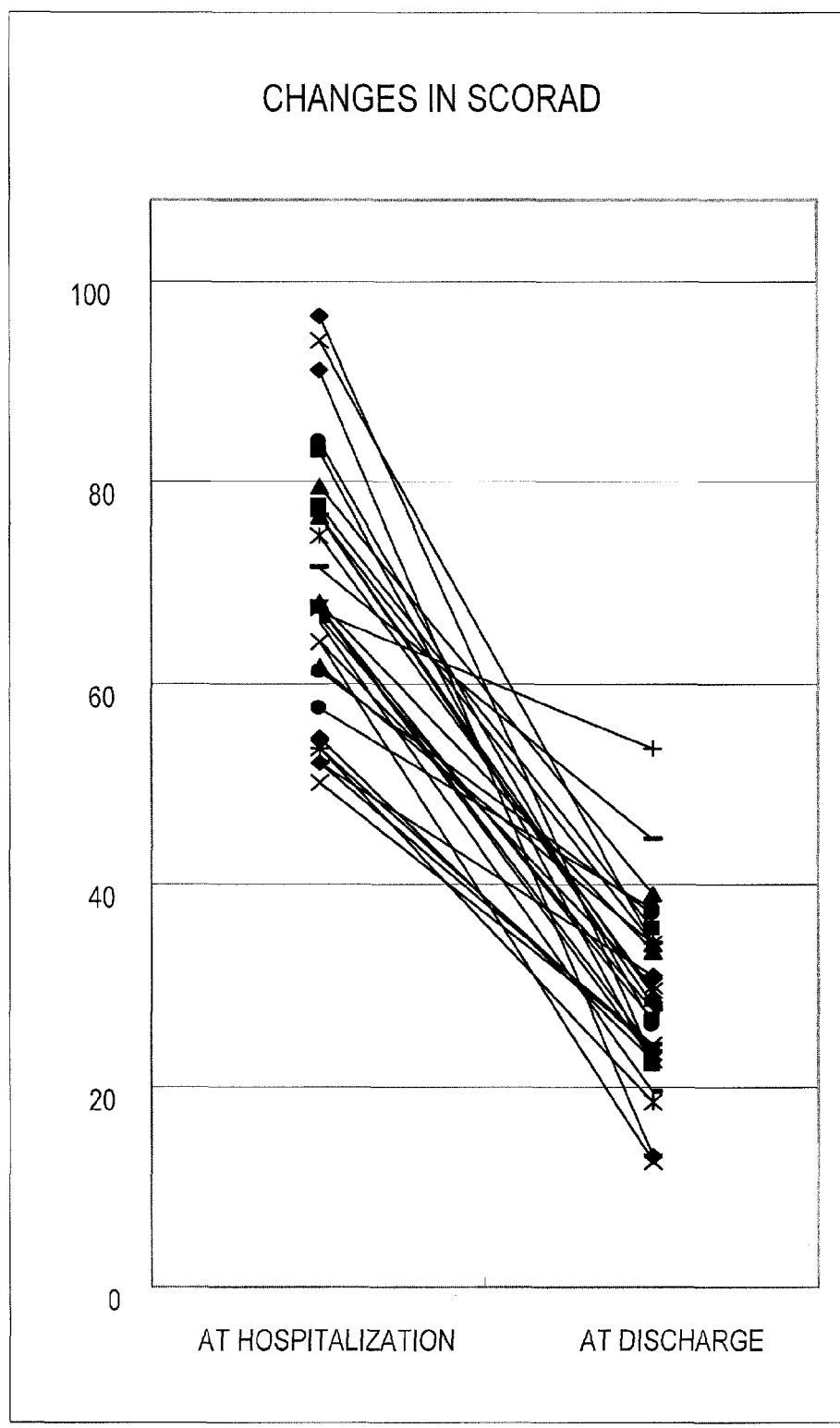
FIG. 1 is a graph showing changes in SCORAD scores at hospitalization and at discharge.

Next, an explanation will be given about the above-described method for treatment of atopic dermatitis and infectious dermatitis with biological spa therapy, with reference to an exemplary embodiment. The embodiment to be described below is illustrated as an example. The present invention is not limited to the embodiment illustrated below, and can be practiced in various modes within a scope not departing from the technical concept as described in the claims.

(1) ABSTRACT

Biological spa therapy (hereinafter abbreviated as BST) has been used to treat atopic dermatitis (AD) at the inventor's hospital since March 2005. *Bacillus* is a bacterium commonly found in aerobic soil in the natural environment. By Sep. 10, 2013, 191 serious AD cases had been treated. A complete response was achieved in 90% patients. As a rule, treatment was performed without the topical use or oral administration of steroids, tacrolimus, or antifungal agents and without the oral administration of cyclosporine.

BST is a type of bacterial therapy that uses bathwater containing fermentation powder of Makomo, a plant native to rivers in Japan, suspended and fermented therein. This powder (*Bacillus* powder) contains $\geq 0.1 \times 10^8$ CFU/g of spores of *Bacillus* bacteria, ensuring that $10^6$-$10^7$ CFU/mL of useful *Bacillus* bacteria are cultured in the bathwater.

Each patient was allocated a separate bathroom and bathed in the cultured bathwater for 2-6 h/day. This treatment was conducted on an inpatient basis over approximately 3 months. This report outlines the outcomes of 30 serious AD patients with scoring atopic dermatitis (SCORAD) scores of $\geq 40$ who underwent BST over a 1-year period. A complete response was achieved, with the SCORAD scores and the serum *thymus* and activation-regulated chemokine (TARC) levels decreasing by 58.6% and 89.8% on average, respectively. Moreover, lactate dehydrogenase levels (LDH) decreased by 86.2%, and thus fell on or below the designated cutoff level. This completely novel and effective natural therapy can be performed at home and could significantly ease the suffering of serious AD patients, in particular, with high probability. Moreover, AD was dramatically improved by contact with the soil bacteria *Bacillus*, and this strongly supports the conventional hygiene hypothesis. Here, the details of the findings will be reported, along with a discussion of the mechanism of action and an explanation of the BST concept.

(2) INTRODUCTION

The incidence of atopic dermatitis (AD) has been increasing worldwide (see References 1 and 2), including in Japan. Many problems associated with AD treatment, such as the treatment of cases not responding to topical steroid therapy and side effects associated with long-term use of steroid, in particular, remain unsolved. The social maladjustment that patients experience physically and mentally because of long-term chronic dermatitis has also been highlighted as a social problem. Recent studies have shown that chronic skin infections due to *Staphylococcus aureus* or the fungus *Malassezia* as chronic antigens can cause chronic allergic reactions in adult AD patients. At present, most AD cases are treated with immunosuppressive therapy that mainly involves topical steroid use. However, this therapy can actually weaken the skin immune system to cause skin fragility, and encourage the growth of pathogenic fungi, as its side effects. In serious AD cases, steroid-resistant tachyphylaxis often occurs, leading to treatment cessation in some cases (see Reference 3).

Probiotics such as *lactobacillus* are commonly used by the general public; however, viable microorganisms are rarely used in the field of medical treatment. Meanwhile, since the 1990s, researchers have looked at the fields of agriculture and bacteriology for useful bacteria that could be found in nature. In the 2000s, many useful bacteria that could be used to combat pathogenic bacteria and fungi in crops were discovered. These organisms were then commercialized worldwide as antimicrobial agents (biotic pesticides), which have been found to be effective. As these biotic pesticides have been recognized as safer both for humans and the environment than conventional chemical pesticides, the range for their use has gradually expanded (see Reference 4).

The plant fermentation powder used in BST has been used as a popular health food since around 1952 in Japan, and contains a large amount of *Bacillus* spores. *Bacillus* is a group of aerobic bacteria that exhibits gram-positive sporulation and is generally observed on the soil surface. In 1945, the antibiotic bacitracin was obtained from *Bacillus subtilis*, which is one of *Bacillus*. This organism has been used as a model organism for genome research, and its entire base sequence was determined in 1997. Along with biotic pesticides, many enzyme preparations have been commercialized. Japanese people consume these enzymes in large amounts through the food called natto (fermented soybeans); the enzymes are considered highly safe (see References 5 and 6).

The inventor himself has been amazed at unbelievable effects of BST. However, since it was a completely novel therapy, the inventor had been hesitant to publish this therapy until the effects and safety thereof were assured. Seeing severe patients isolated from society cured one after another, the inventor felt that this therapy should bring benefits to many serious AD patients. That is why the inventor has decided to file this application.

BST is an extremely effective treatment method that may also offer many clues regarding the relationship between human immunity and soil bacteria.

(3) SUBJECTS AND METHODS

This study included 30 serious AD patients (male: 15, female: 15; mean age: 30 years) with SCORAD scores of ≥40 who were admitted to the inventor's hospital at some time during a period of two years from Feb. 1, 2010; these patients underwent BST for ≥1 month. The mean disease duration was 22 years, with onset occurring during infancy in 21 cases (70%), between 7 and 19 years of age in 4 cases (13%), and at ≥20 years of age in 5 cases (17%).

Each patient was allocated a separate bathroom to use and bathed in cultured bathwater for 2-6 h/day. The mean number of hospitalization days was 92.

All subjects had previously been treated with long-term topical steroids, and many of them had undergone some type of alternative medicine.

As a concurrent treatment, some subjects with significant symptoms such as pruritus or erythema were taking antiallergic agents, herbal medicine orally, and/or non-steroidal agents topically. However, no subject was using topically or orally administered steroids, topically administered tacrolimus, oral immunosuppressants such as cyclosporine, or topically or orally administered antifungal agents.

Rebound caused by the discontinuation of immunosuppressant agents was observed in approximately 50% patients after hospitalization.

During hospitalization, traditional Japanese meals mainly consisting of vegetables and fish were provided, and approximately 50% patients ate brown rice as a staple food.

In specific IgE (CAP) test (see Table 1), the results are as follows: *Malassezia* positive rate of 100% with average sensitivity of 27.2 $U_A$/ml, mites positive rate of 96.7% with average sensitivity of 426.4 $U_A$/ml, cedar pollen positive rate of 96.7% with average sensitivity of 104.6 $U_A$/ml, *Candida* positive rate of 90.0% with average sensitivity of 23.0 $U_A$/ml, Staphylococcal enterotoxin A positive rate of 80.0% with average sensitivity of 3.6 $U_A$/ml. The positive rates of true fungi normally present in the skin such as *Malassezia* and *Candida*, which are chronic antigens, are high, which is considered to be a characteristic of adult AD.

TABLE 1

| | *Malassezia* | mites | cedar | *Candida* | *Trichophyton* | *Aspergillus* |
|---|---|---|---|---|---|---|
| Positive rate (%) | 100.0 | 96.7 | 96.7 | 90.0 | 89.7 | 86.7 |
| Sensitivity ($U_A$/mL) | 27.2 | 426.4 | 104.6 | 23.0 | 13.9 | 14.1 |

| | *Cladosporium* | Brewer's yeast | food | *Penicillium* |
|---|---|---|---|---|
| Positive rate (%) | 85.0 | 84.6 | 83.3 | 83.3 |
| Sensitivity ($U_A$/mL) | 8.0 | 10.8 | 23.3 | 8.0 |

| | *Staphylococcus aureus* A | *Staphylococcus aureus* B | *Poaceae* | weed |
|---|---|---|---|---|
| Positive rate (%) | 80.0 | 79.3 | 75.9 | 72.4 |
| Sensitivity ($U_A$/mL) | 3.6 | 5.4 | 6.0 | 32.2 |

(4) RESULTS

The effects of BST were assessed according to SCORAD scores (0-103) (see Reference 7) and the objective blood markers [*thymus* and activation-regulated chemokine (TARC) levels (cutoff level: 450 pg/mL), lactate dehydrogenase (LDH) levels (245 U/L), eosinophil percentage (7%), and IgE levels (170 IU/mL)].

One of the 30 patients was excluded from the LDH evaluations because of the development of temporary hepatitis of unknown causes.

Figure 2:
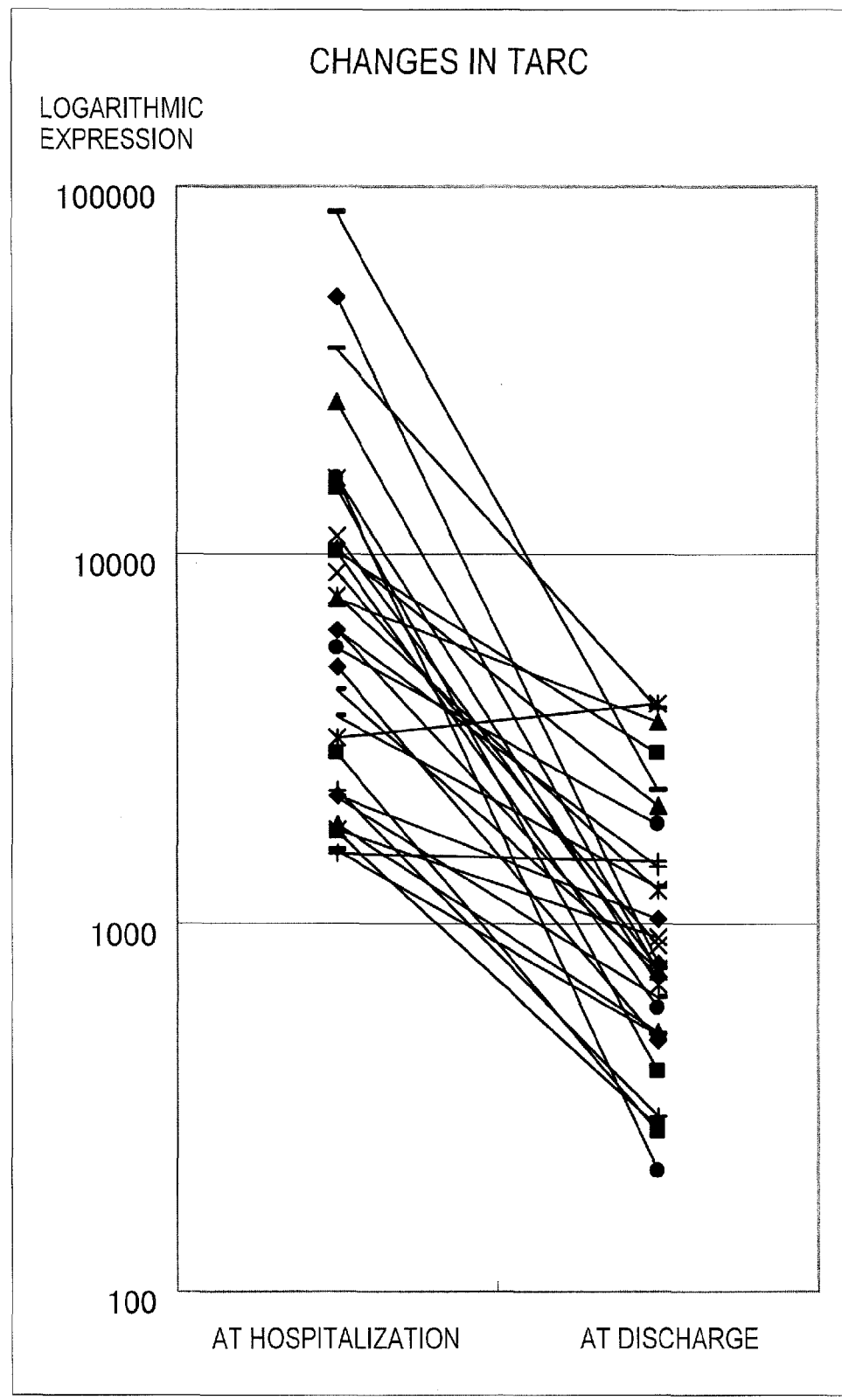
FIG. 2 is a graph showing changes in TARC levels at hospitalization and at discharge.

The mean SCORAD score was 69.3 at hospitalization and 28.7 at discharge, demonstrating a decrease of 58.6% (n=30; p<0.01) (see FIG. 1). The mean TARC level was 12,107 at hospitalization and 1,239 at discharge, which was a decrease of 89.8% (n=30; p<0.01). A complete response (improvement in the TARC level of ≥70%) was evident in 76.7% of these cases (see FIG. 2).

Figure 3:
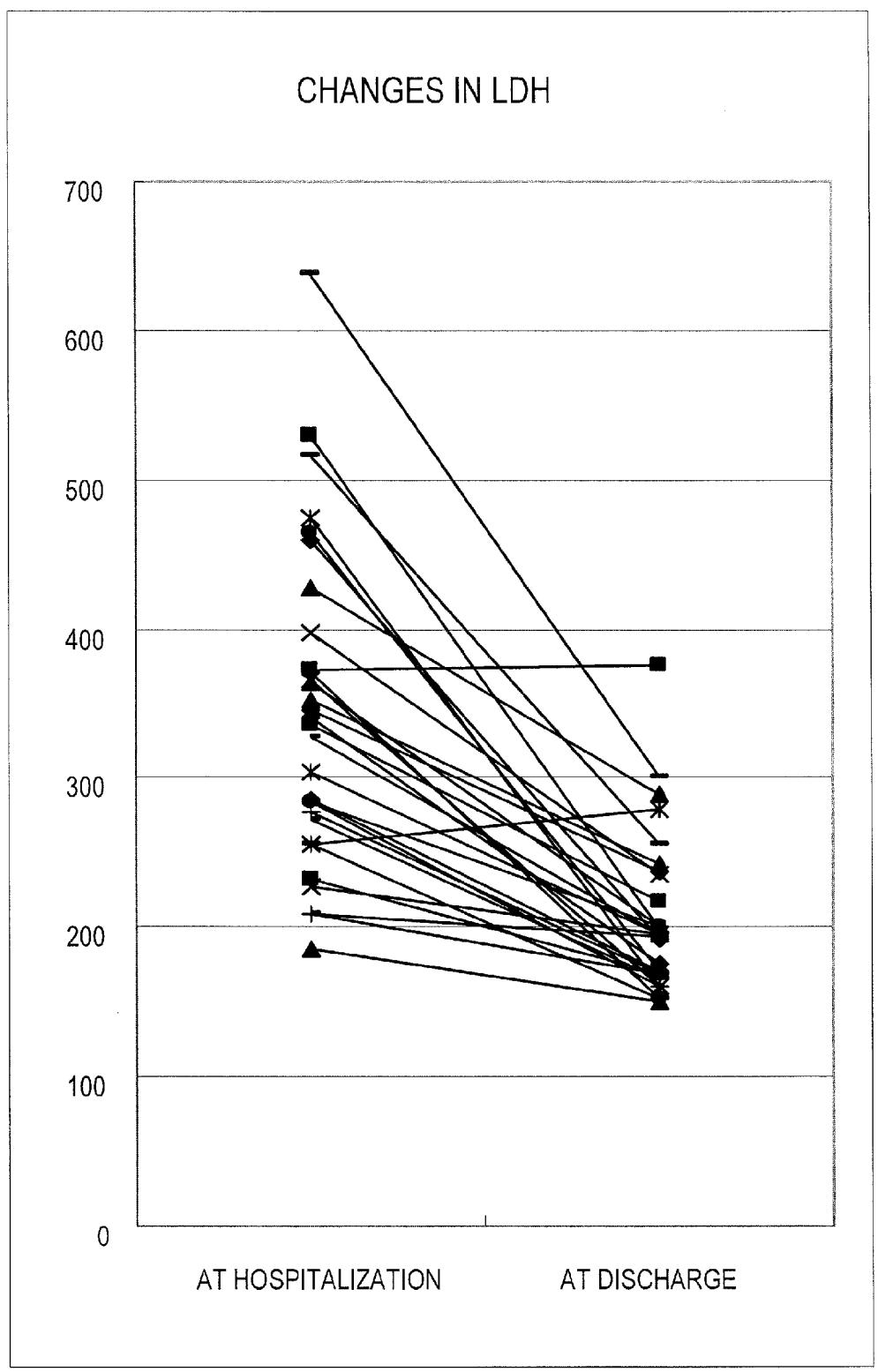
FIG. 3 is a graph showing changes in LDH levels at hospitalization and at discharge.

The mean LDH level was 345 at hospitalization and 198 at discharge; this represents a decrease of 42.4% (n=29; p<0.01). A complete response (improvement to the cutoff level of 245 or less) was evident in 86.2% of these cases (see FIG. 3).

Figure 4:
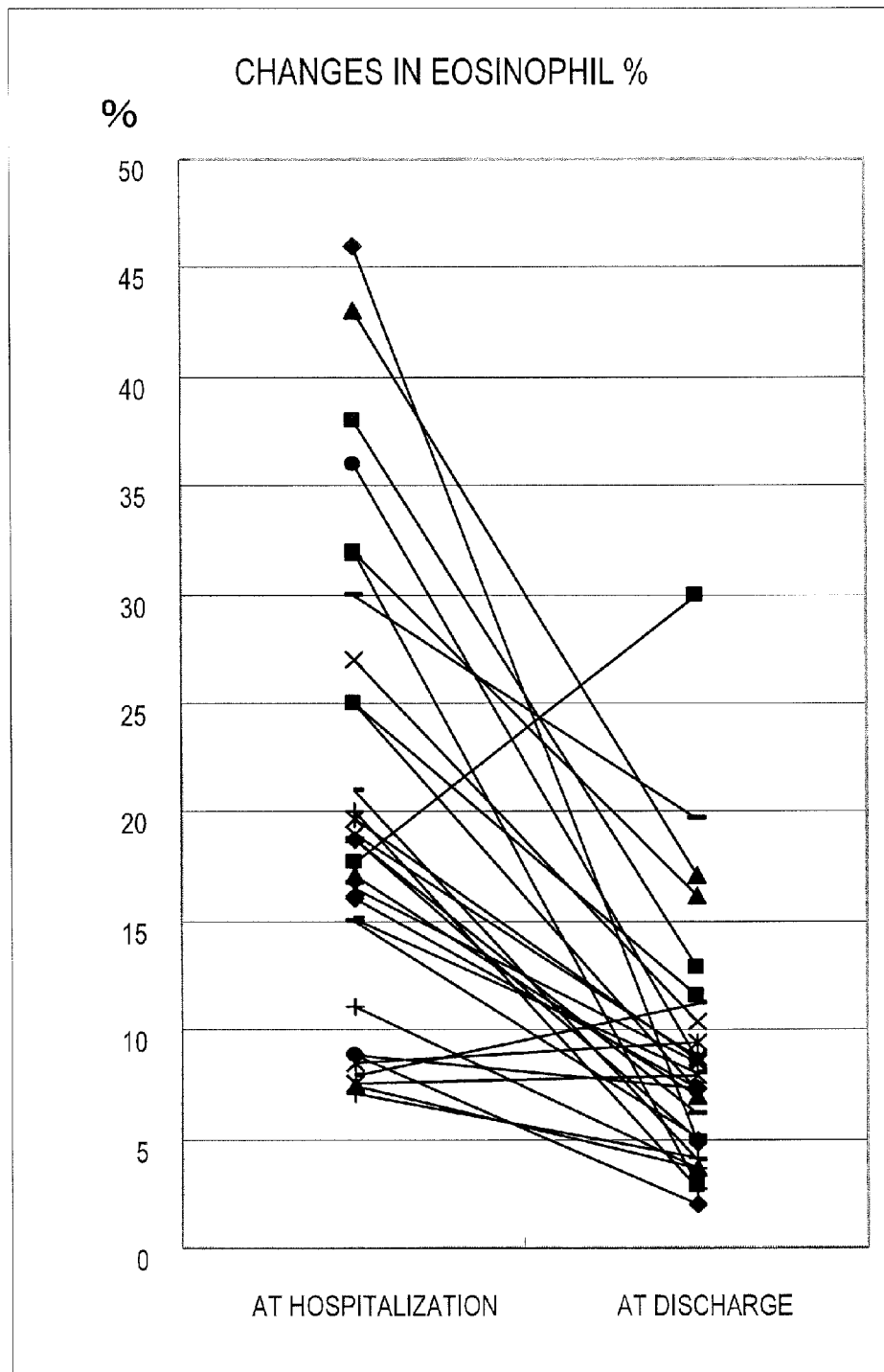
FIG. 4 is a graph showing changes in eosinophil percentage at hospitalization and at discharge.

The mean eosinophil percentage was 20.5% at hospitalization and 8.7% at discharge, demonstrating a decrease of 57.8% (n=30; p<0.01). A complete response (reduction to lower than or equal to 50% of the previous level) was evident in 66.7% of these cases (see FIG. 4).

The mean IgE radioimmunosorbent test (RIST) level was 12,535 at hospitalization and 9,595 at discharge, thus decreasing by 23.5% (n=30; p<0.01).

Significant improvements were observed in SCORAD scores and all four blood markers, with the majority of cases exhibiting a complete response.

Figure 5:
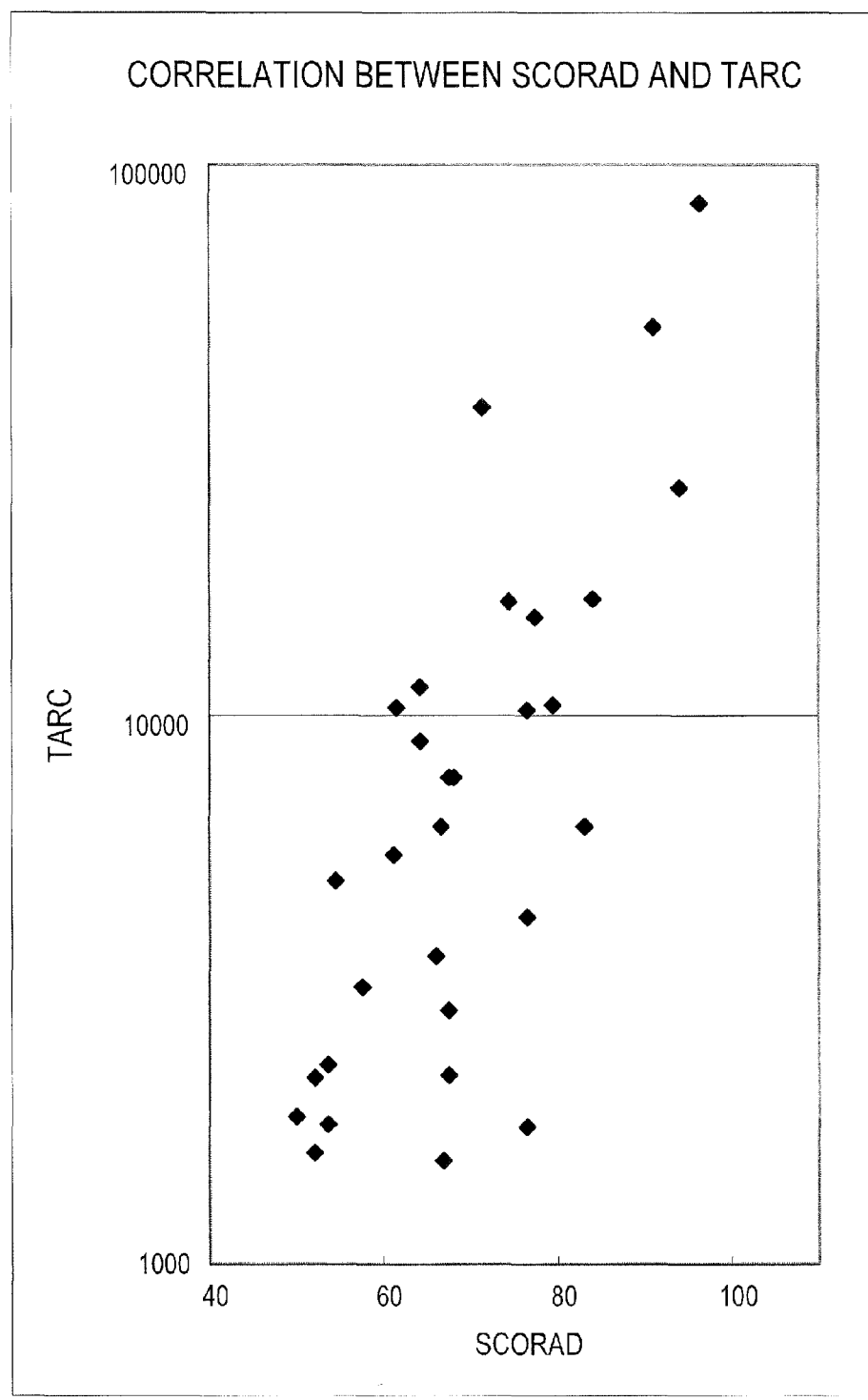
FIG. 5 is a graph showing a correlation between the SCORAD scores and TARC levels.

Possible correlations between the four blood markers and SCORAD scores at hospitalization were investigated. The correlations with the TARC levels, LDH levels, IgE levels, and eosinophil percentage were r=0.66 (p<0.01) (see FIG. 5), r=0.54 (p<0.01), r=0.38 (p<0.05), and r=0.27 (p≥0.05), respectively. This indicated correlations with the TARC and LDH levels. The strongest correlation was observed with the TARC levels, which appeared to be sensitive to changes in dermatitis. Thus, these levels were useful for assessing treatment. The improvement rates also showed correlations between the SCORAD scores and both TARC (r=0.53; p<0.01) and LDH levels (r=0.50; p<0.01).

Although the SCORAD scores improved in all subjects, subjects with improvements of <30% in the SCORAD scores and TARC levels were considered non-effective cases when taking into consideration the improvement effects by hospitalization itself. Therefore, 28 of 30 cases were effective cases, which amount to 93.3%.

At discharge, most patients no longer required oral or topical medicines; however, dermatitis was exacerbated in many patients who did not continue BST after discharge. Dermatitis improved further in patients who were able to continue BST after discharge. In some of these cases, the TARC levels, eosinophil percentage, and LDH levels were all normalized and AD completely disappeared; the IgE levels also decreased markedly in those patients (Case presentation: Nos. 3 and 10).

(5) NON-EFFECTIVE CASES AND SIDE EFFECTS 2 of 30 cases (6%) were non-effective cases; i.e., no improvement was observed in terms of both SCORAD scores and TARC levels. In 3 of 30 cases (10%), side effects were observed that forced discontinuation of BST. In 1 of the three such cases, eczema began to occur on the legs due to stimulation by bathing; therefore, BST was discontinued. Side effects observed in the other 2 of the three such cases were an increase in the eosinophil percentage (38-47% of WBC) and allergic generalized erythema, which was accompanied by fever and rubefaction. Therefore, BST was discontinued. Both cases improved after discontinuing the therapy without any additional treatment, and one of the patients restarted BST 1 week later. The remaining patient did not undergo any further BST, but the rash was better than that before undergoing BST. In sum, side effects requiring BST discontinuation occurred in only 2 cases (6%).

(6) CASE PRESENTATION

TABLE 2

|  | Normal levels | 2010 Jun. 15 | July 22 | August 28 | September 6 | October 23 | December 25 | 2011 Apr. 22 | November 19 | 2012 Jun. 29 | November 17 | 2013 May 17 |
|---|---|---|---|---|---|---|---|---|---|---|---|---|
| TARC | ≤450 | 10340 | 2834 | 3275 | 2076 | 1552 | 345 | 272 | 227 | 290 | 205 | 173 |
| LDH | 120-245 | 427 | 387 | 347 | 289 | 238 | 139 | 152 | 152 | 136 | 140 | 124 |
| IgE | ≤170 | 7253 | 6385 | 4295 | 3848 | 4498 | 3904 | 2186 | 1738 | 996 | 799 | 674 |
| Eosinophil | ≤7% | 17.1 | 8.2 | 7.4 | 7.0 | 5.5 | 1.0 | 0.9 | 1.3 | 3.3 | 1.9 | 1.8 |

[Case A; 45-Year-Old Female; Hospitalization Period: Jun. 15, 2010-Sep. 12, 2010; SCORAD Score: 79.5 at Hospitalization and 39.0 at Discharge]

Figure 15A:
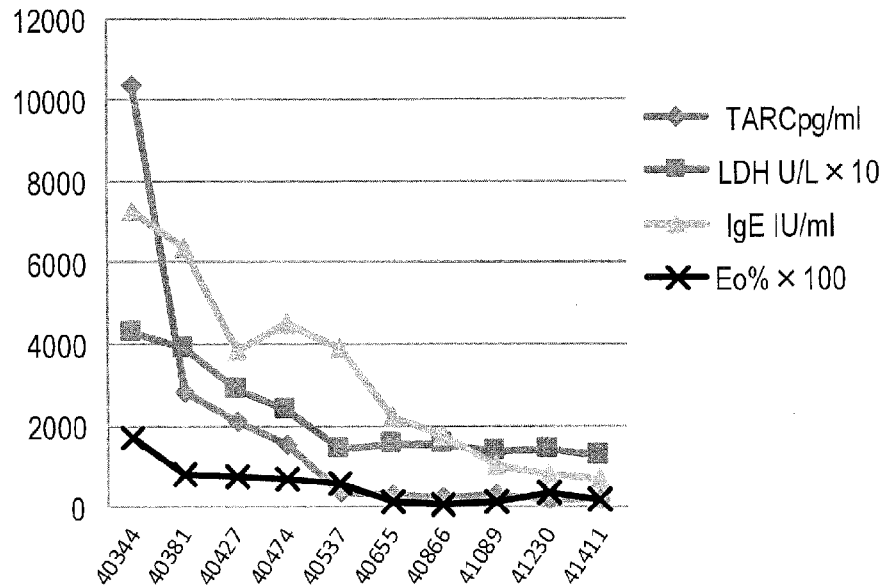
FIGS. 15A and 15B are graphs showing cases.
Figure 15B:
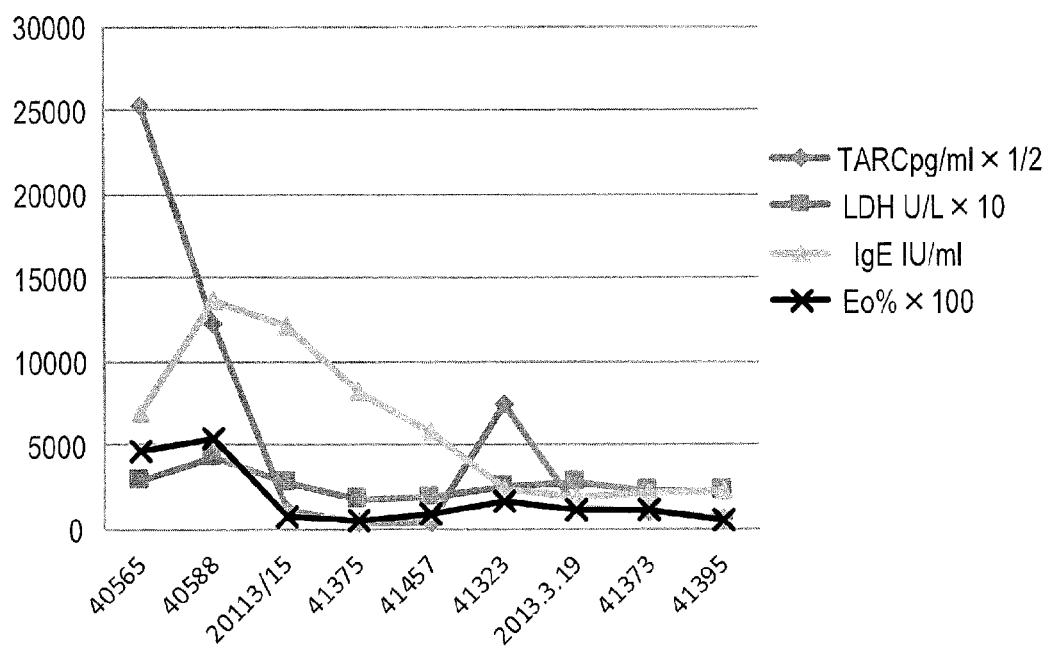

The onset of AD occurred at 3 years of age in this patient. From 18 years of age, the patient underwent the topical administration of steroids and tacrolimus for generalized dermatitis; however, the symptoms were not well controlled. The generalized dermatitis had been persistent and did not improve despite the patient undergoing various types of alternative therapies. Starting in May 2010, the symptoms worsened further with persistent chills, and the patient was no longer able to engage in work duties. On Jun. 15, 2010, she was hospitalized at the inventor's hospital and began BST. After 3 months, a complete response was achieved; the patient continued to undergo BST at home after discharge. From October 2010, the patient no longer required any treatments other than BST and by Dec. 25, 2010, all inflammatory markers such as TARC were normalized. Her skin is currently in a healthy state, and the TARC and IgE levels have continued to drop (see Table 2 and FIG. 15A).

oral steroids; however, his condition gradually deteriorated, with rubefaction and effusion changes mainly over his trunk. In January 2011, he began oral antibiotics and steroid injections; however, little improvement was observed in his skin condition. The patient was unable to move because of strong rubefaction, swelling, strong effusion changes, pain, and strong itching over his entire body; he was then hospitalized at the inventor's hospital. Because the patient was methicillin-resistant *S. aureus* (MRSA)-positive and had a persistent slight fever, BST was not started when he was first hospitalized. Orally administered antibiotics and vancomycin ointment were used but no improvement was observed. BST was initiated in February 10, and marked improvements in skin symptoms were observed on and after the following day. One month later, TARC and eosinophils had decreased to 1/10. The patient continued BST at home for 6 months after discharge but then discontinued the therapy as AD symptoms had completely disappeared. In February 2013, the patient was hospitalized again because of relapse. Once again, symptoms improved with BST alone, without any additional medication, and the patient was discharged to return to work. The patient will continue BST at home (see Table 3 and FIG. 15B).

(7) DISCUSSION

TARC, which is a chemokine produced by keratinocytes, dendritic cells, and platelets, is a blood marker that sensitively reflects the state of AD disease (see References 8, 9, and 10). Tamaki, K et al. reported that the serum TARC correlates with the SCORAD score for skin symptoms, with 1523±243 indicating mild severity, 2598±409 indicating moderate severity, and 8009±995 indicating strong severity. In the present study, TARC levels also reflected the disease state, with patients in the severe group exhibiting higher TARC levels.

Adult AD can be caused by antigens external to (outside of) the skin such as mites, pollen, and pets, or by antigens

TABLE 3

|  | Normal levels | 2011 Jan. 22 | February 14 | March 15 | April 11 | July 2 | 2013 Feb. 18 | March 19 | April 9 | May 1 |
|---|---|---|---|---|---|---|---|---|---|---|
| TARC | ≤450 | 50457 | 24409 | 2082 | 772 | 623 | 14905 | 2560 | 1922 | 1139 |
| LDH | 120-245 | 286 | 424 | 271 | 170 | 183 | 248 | 280 | 227 | 226 |
| IgE | ≤170 | 6949 | 13622 | 12080 | 8172 | 5827 | 2385 | 1860 | 2165 | 2172 |
| Eosinophil % | ≤7% | 46.0 | 54.0 | 6.9 | 4.8 | 8.4 | 16.0 | 11.2 | 10.7 | 5.2 |

[Case B; 29-Year-Old Male; Hospitalized Twice; First Hospitalization Period: Jan. 22, 2011-Apr. 21, 2011; SCORAD Score: 91 at Hospitalization and 13 at Discharge; Second Hospitalization Period: Feb. 18, 2013-Apr. 13, 2013]

For this patient, AD first appeared in infancy but improved during school age and thereafter. In May 2009, AD appeared mainly on the patient's face and could not be controlled with topical steroids alone. The patient also took internal to (inside of) the skin (within cuticle, hair follicle, or the like) such as *Malassezia* and *Candida* infecting the skin, which are *S. aureus* or yeast-like fungi. Chronic infections caused by pathogenic fungi accompanied by a biofilm can form an internal skin antigen that causes perennial allergies, which can then lead to adult AD.

In particular, recent studies have shown significantly higher detection rates of *S. aureus* in AD patients than in patients with other types of dermatitis. It has been suggested that enterotoxin, which is produced by *S. aureus*, works as a super antigen to stimulate immune cells. This means it could be heavily involved in the onset of AD (see References 3 and 11). Topical and oral administration of antibiotics may be used as a treatment; however, this often only leads to a temporary improvement followed by acquisition of tolerance and new problems such as MRSA infection. The antiseptic, povidone-iodine, also offers some improvement in AD but has little effect on moisture lesions and can also be a skin irritant. Meanwhile, the spread of resident skin fungus such as *Malassezia* or *Candida* is also considered a significant cause of AD. As the strains of *Malassezia* can now be classified (see Reference 12) and advances in technology have made it possible to analyze the DNA of difficult-to-culture bacterial strains directly from the skin, AD-specific bacterial strains can now be identified. In Japan, *Malassezia* strains such as *M. globosa* and *M. restricta* in particular are considered causative strains for AD (see Reference 14). *Malassezia* infection appears to have a particularly strong effect on patients with head and neck AD, making the topical and oral administration of antifungal agents effective (see Reference 13). It has been reported that in some cases these antifungal agents can work effectively when combined with steroids or tacrolimus. However, it is difficult to control symptoms with antifungal agents alone in the actual treatment and, especially, long-term effects cannot be expected. While it is known that the inhibition of the causative bacteria that forms the allergen from infecting the skin could treat the actual cause of the disease, no clear treatment method has been discovered. While in many cases, physicians have no other options besides symptomatic treatment involving suppression of the skin immune system by topical steroids or tacrolimus, the long-term use of which can increase pathogenic microbial infection and lead to treatment resistance by the decreased skin barrier capacity. Many patients have no choice but to undergo oral administration of steroids or cyclosporine; however, dosage reduction and/or drug cessation can then become difficult, with long-term usage then putting patients at risk of systemic side effects. For AD patients, BST is a highly safe and effective method of therapy that does not require medication. It could also open up new possibilities for understanding the causes of AD and for treating AD.

Possible mechanisms for the effects of bacterial therapy include the competition for ecological dominance among microbes, the production of chemical substances for the inhibition of other microbes, and the induction of changes in patients' immune systems.

Characteristics of BST include the low likelihood of bacterial resistance, its safety and low impact on the human body, and the milder and thus more time-consuming effects than those caused by chemical substances. In addition, this treatment requires that the environmental conditions for allowing the useful microorganisms to function are correctly set up.

*Bacillus* has strong reproductive power, exhibiting competitive action that inhibits destructive fungi. It also secretes antibacterial active peptides (iturin A, plipastatin, etc.) and surfactin, which exhibits a strong surface action. It is known that, in such a manner, *Bacillus* breaks down the biofilm of destructive fungi and inhibits the reproduction of many plant pathogenic bacteria and fungi (see References 4 and 5).

The greatest effect of BST appears to be the inhibition of *Staphylococcus aureus, Candida albicans*, and *Malassezia* by *Bacillus* in the bath liquid. These effects of inhibition were also tested in vitro and clear results were obtained (see Supplement 1 to be described later).

With BST alone, ≥90% of serious AD cases exhibited dramatic improvement, with the skin returning to its original healthy state. Therefore, it appears that the greatest causative allergens for adult AD are pathogenic microbes, which are allergens internal to (inside of) the skin.

BST is a safe and extremely effective natural therapy, but its main disadvantages are the time and effort required. Subjective symptoms may be alleviated within days or take 2 months to improve. Serum TARC is a good marker as it may exhibit changes before the subjective symptoms improve. For serious cases, BST could become first-line treatment and be used in a complementary manner to conventional treatments. For mild cases, BST could be used in a complementary manner if conventional treatments lead to exacerbations.

The efficacy and safety of BST need to be tested in many countries throughout the world. In addition, BST could be used in infants to contribute to the formation of a healthy immune system; however, clinical examples of this are scarce at present.

(8) RELATIONSHIP BETWEEN BST AND THE HYGIENE HYPOTHESIS

*Bacillus*, which works as the useful bacteria in BST, is a common type of bacteria widely found in soil.

AD became more common in Japan approximately 40 years ago, before which it was almost non-existent. It was around this time that soil rapidly disappeared from people's daily lifestyles with the rapid development of Japan's economy.

Most of the nation's population was previously in daily contact with soil through agriculture, in particular, rice farming, which had flourished in Japan.

Houses were also made of wood, with mud walls and earth floors; peoples' clothing was often covered with soil; and roads were dirt roads surrounded in clouds of dust.

People used to constantly come in contact with *Bacillus*; however, these surfaces are now covered with chemical substances and asphalt, with dirt even disappearing from school grounds. Because of lack of contact with soil, proper skin immune systems are not formed during infancy. It seems that *Bacillus*, which previously inhibited pathogenic fungi, has thus disappeared from our living spaces and skin.

Each gram of soil is said to have $10^4$-$10^{10}$ bacteria, with DNA research using uncontaminated soil indicating close to 1 million different strains per gram (see Reference 18).

People previously had frequent interactions with dirt from infancy, and their immune systems developed through contact with soil bacteria.

In particular, Th1 natural immunity has existed as an immune system since ancient times and is believed to develop through activation via contact with its "rivals," i.e., many types of bacteria. Have we administered only several types of vaccinations but neglected 1 million types of natural vaccinations?

Diets have also undergone significant changes. What is most noticeable is the fact that fat intake in Japan has tripled over the past 40 years (see Ministry of Health, Labour and Welfare: Trends in Nutrient Intake). Increased fat intake promotes the excessive growth of *Malassezia*, a lipid-requiring resident fungus, on the skin; this growth could have contributed to the increased incidence of AD.

As humans are primarily part of nature, the artificial environments brought about by advances in civilization appear ill-suited to our survival. The great earthquake and tsunami disaster and subsequent nuclear contamination in Japan along with global warming are signs that the human race needs to regain its humility and rethink how it should interact with nature. As per the saying, "not seeing the forest for the trees," could an exit from the cytokine forest, in which we have been lost, be found by taking a wider overall viewpoint of AD treatment? Learning from our past lifestyles could be a simple way to benefit both humans and nature.

As per the saying "not seeing the forest for the trees", could an exit from the cytokine forest, in which we have been lost, be found by taking a wider overall viewpoint of AD treatment? Learning from our past lifestyles could be a simple way to benefit both humans and nature.

(9) OUTLINE OF BST

The scientific name of the plant, Makomo, which was used as the main ingredient of *Bacillus* powder for BST, is *Zizania latifolia* Turcz. Makomo is a perennial plant, closely related to rice, that can be widely found on freshwater shores throughout all regions of East Asia, including Japan. Varieties of Makomo found on the American continent are called wild rice or Indian rice, and the seeds are used as natural foods. In Japan, the seeds have long been eaten while the leaves have been used in sacred ceremonies since ancient times. Makomo was first fermented and used as a health food by the public in Japan around 1952. Thousands of users of the plant take several grams of it each day, without reports of significant health problems. Furthermore, around 1970 at the latest, some enthusiasts suspended the fermentation powder in their bathwater and bathed therein. While this spa therapy was also being conducted for AD, the inability to obtain reliable results impeded its spread as a treatment method. The oral administration of fermented Makomo powder was attempted at the inventor's hospital but AD exacerbated in most patients. It appeared that bacteria in bathwater were mainly responsible for their effects on AD. Therefore, the fermentation powder was improved and a water quality control system was developed and improved in the inventor's hospital. This created stable *Bacillus* culture and water quality conditions that improved the treatment effects.

BST involves suspending approximately 200-400 g of fermentation powder in 150 L of bathwater contained in a bathtub. A specialized circulation system is used to enable sufficient temperature control and aeration. This stimulates the aerobic reproduction of useful bacteria, leading to secondary fermentation. After approximately 1 week, the water quality stabilizes and the spa treatment can be initiated. This fermentation liquid is changed once every 1-2 months in the acute phase of dermatitis and once every 2-3 months in the chronic phase of dermatitis, while considering the improvement state of dermatitis and the concentration of ammonium ion and nitric acid.

Many of the naturally occurring heterotrophic bacteria such as *Bacillus* in the fermentation powder exhibit high heat resistance and spore formation when growth conditions deteriorate. BST bathwater contains many heterotrophic bacteria ($10^6$-$10^7$/mL) including various *Bacillus* types such as *B. subtilis, circulans, B. licheniformis*, and *B. sphaericus*. The bacterial types present in the typical bathwater will be presented in Supplement 2 to be described later.

None of the heterotrophic bacteria in the bathwater have clearly caused an infection at the inventor's hospital; thus, they appear to have extremely low pathogenicity. The bathwater is opaque and brown in color. The bathwater is partially changed after 3 months have passed. Until then, the water is continually used without being changed. The water quality is stable because the minerals and organic matter from the patients' skin such as keratin and waste products are used as sources of nutrients for the microbes. Bathing every day in the useful *Bacillus* culture liquid improves the skin of adult AD patients because it decreases the number of resident pathogenic bacteria on the skin that can form allergens while it stimulates the Th1 natural immune system of the skin. Many patients have said that their itching and dryness symptoms improved directly after the first bathing. The effects are more marked for patients who have strong infections with pathogenic bacteria causing wide-ranging ulceration, erythema, and mild fever accompanied by effusion. Longer bathing time increases the effects; bathing for about 4 h is recommended in the acute phases of the disease. Bath temperature should be 35° C.-42° C.

BST needs to be performed on a continuous basis because the patient's allergic constitution may not necessarily have been cured even if the AD symptoms appear to have once completely improved; therefore, a relapse of AD could occur if treatment is discontinued. However, once the skin symptoms have decreased and the patient has recovered normal skin function, bathing for long periods is no longer required. At this point, the skin condition can be maintained with 10 min of bathing per day.

Even if BST is continued, dermatitis may still be exacerbated by antigens external to (outside of) the skin, such as mites, pollen, and pets. Conversely, greater effects can be expected for cases with high specific IgE (CAP) levels for typical adult AD allergens, fungi such as *Malassezia* or *Candida*, and *S. aureus*.

Moreover, effects observed for patients who underwent BST at home on an outpatient basis were clear, despite these effects being smaller than those observed for patients who underwent the therapy on an inpatient basis.

The following are required for maintaining safety: (1) an individual bath should be allocated for each patient; (2) only specialized *Bacillus* powder with confirmed safety should be used; and (3) a circulation system should be installed to properly set up the culture conditions such as water volume, temperature, and oxygen. With the bath and the circulation system, not only useful *Bacillus* is cultured but also degradative treatment of organic matter such as the *Bacillus* powder and bodily secretions is performed to maintain the water quality.

If conditions deteriorate, harmful decomposition products such as ammonia ($NH_3$), hydrogen sulfide ($H_2S$), methane ($CH_4$), mercaptan, and a lower fatty acid such as propionic acid and N-butyric acid may be produced. This will reduce the water quality and cause pathogenic microbes to develop, which could then exacerbate dermatitis.

(10) DISCUSSION REGARDING SAFETY

Over 8 years, in 159 safety tests, *Legionella pneumophila* has never been detected. This is the most feared pathogenic bacterium that may cause infection in this bathwater.

The safety tests used a culture liquid created by suspending an isoconcentration of the fermentation powder in the bathwater and culturing it for 1 week. An acute toxicity test using medaka fish, an oral administration test with 26 volunteers, and a *L. pneumophila* propagation test were performed to test safety. Other microbes that could cause infections will be discussed in Supplement 3 to be described later.

(11) SIDE EFFECTS IN ALL CASES

Including the aforementioned 3 cases, BST caused dermatitis exacerbation in 8 (4.0%) of the 191 AD cases that had undergone BST up to Sep. 10, 2013 at the inventor's hospital. In 5 of these cases (2.6%), this exacerbation involved allergic generalized erythema accompanied by elevated eosinophils, fever, and reddening. Three cases improved with BST discontinuation, while 2 cases were treated with antibiotics and steroids for several days. Two of the 5 cases restarted BST; however, 3 cases were not able to restart therapy. Two of the 3 cases that did not restart the therapy also had depression and were being administered selective serotonin reuptake inhibitor (SSRI) drugs at the same time for mental instability.

Some temporary instances of dermatitis exacerbation and mild rash over the course of treatment were often observed.

(12) CONCLUSION

Bacillus Spa Therapy (BST), which utilizes Bacillus bacteria that can normally be found in aerobic soil in the natural environment, has been used at the inventor's facility for 8 years since 2005 to treat Atopic dermatitis (AD) cases. By Sep. 10, 2013, approximately 191 serious adult AD patients had undergone approximately 3-month long hospitalization for treatment, with complete responses achieved in about ≥90% cases. As a rule, treatment was performed without the topical use or oral administration of steroids, tacrolimus, or antifungal agents and without the oral administration of cyclosporine. BST is a completely new method of bacterial therapy that is highly effective and safe. In contrast to conventional symptomatic treatments, its mechanism of action involves Bacillus-mediated inhibition of Malassezia and S. aureus, the most common allergens in adult AD, and their immune reactions in the skin. It works to complement the weakened resistance of the skin's immune system of AD patients against pathogenic microbes. As this natural therapy can be safely performed at home, it could be especially beneficial to serious AD patients for whom pharmacotherapy has ceased to be effective. Combining this therapy with conventional treatment methods could also help to greatly reduce drug dosages. The introduction of a new field of medicine through this therapy will also increase treatment options.

In future, more studies need to be conducted domestically and overseas to confirm the effects and safety of BST, to investigate its use for pediatric patients, and to evaluate the use of different useful bacteria. This natural and simple therapy teaches us the importance of bringing nature and dirt back into our daily lifestyles.

(13) SUPPLEMENT 1: IN VITRO SUPPRESSION TEST OF A PATHOGENIC FUNGUS BY BACILLUS

A competitive inhibition assay of *Staphylococcus aureus*, *Candida albicans*, and *Malassezia sympodialis* colonies isolated from the skin of AD patients was performed using liquid culture medium to confirm the effects of *Bacillus* in BST bathwater. For *S. aureus* and *C. albicans*, an inhibition zone formation test using solid medium was also performed (Tests Nos. 1, 2, and 3).

(13.1) Test No. 1: *Staphylococcus aureus* Suppression Test (13.1.A) Competitive Inhibition Assay with *Staphylococcus aureus*

Figure 6:
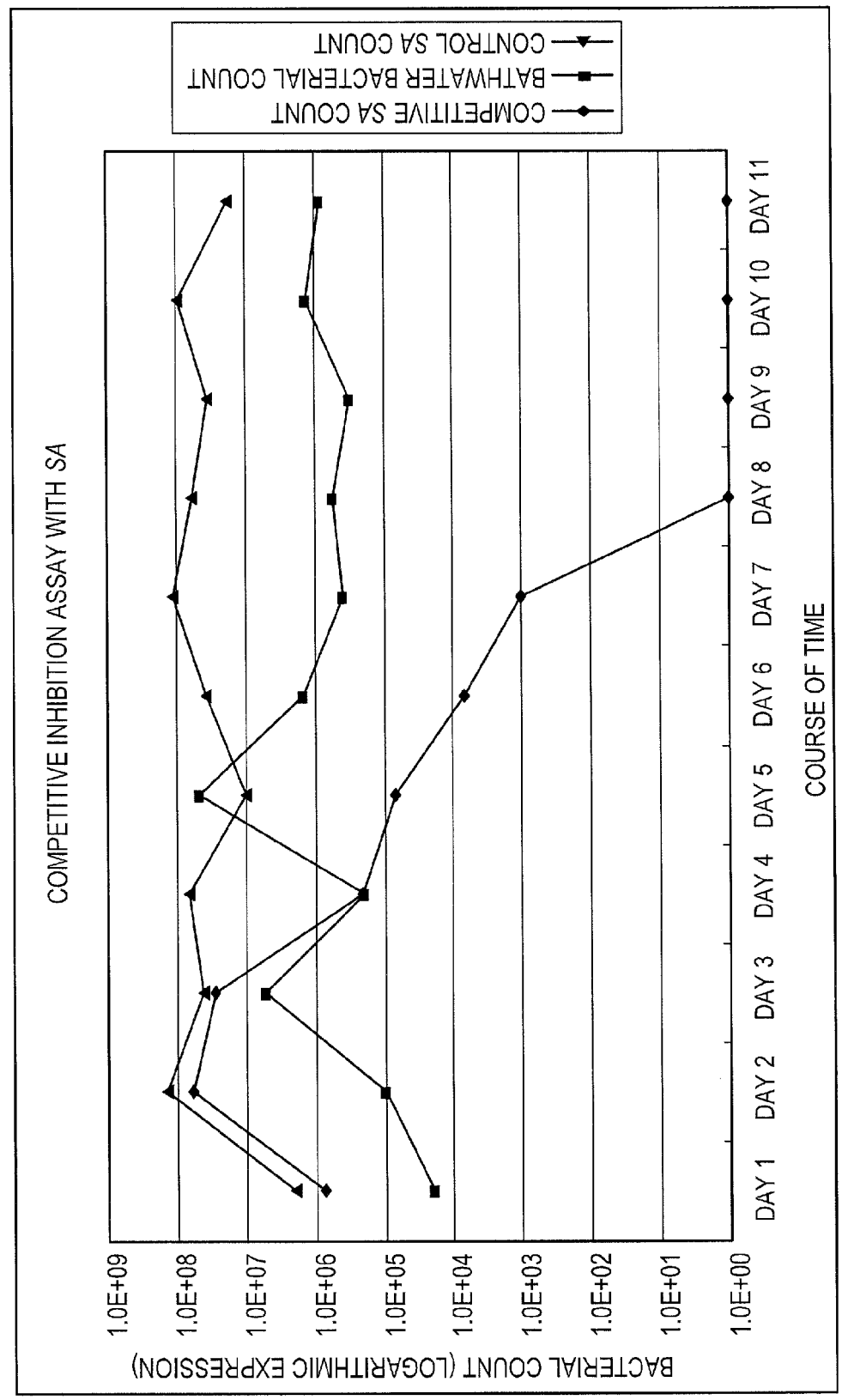
FIG. 6 is a graph showing a result of a competitive inhibition assay with *Staphylococcus aureus*.

An *S. aureus* colony was isolated from the skin of an AD patient on a mannitol salt agar medium with egg yolk (MSEY agar medium) and cultured in a general broth medium for 3 days. One milliliter of *S. aureus* solution ($1\times10^7$/mL) and *Bacillus* culture solution (0.4 g of fermented Makomo powder was suspended in 100 cc of water and aerobically cultured for 2 weeks at 36° C. in order to achieve the same concentration as the bathwater) ($1\times10^7$/mL) were mixed, by 1 mL, in a 200 cc of broth medium and spinner-cultured at 36° C. to perform a competitive inhibition assay. *S. aureus* was cultured alone as a control using the same method. *S. aureus* had completely disappeared on the $8^{th}$ day (see FIG. 6). It is to be noted that *S. aureus* is abbreviated as "SA" in the drawings.

(13.1.B) Inhibition Zone Formation Test

Figure 7:
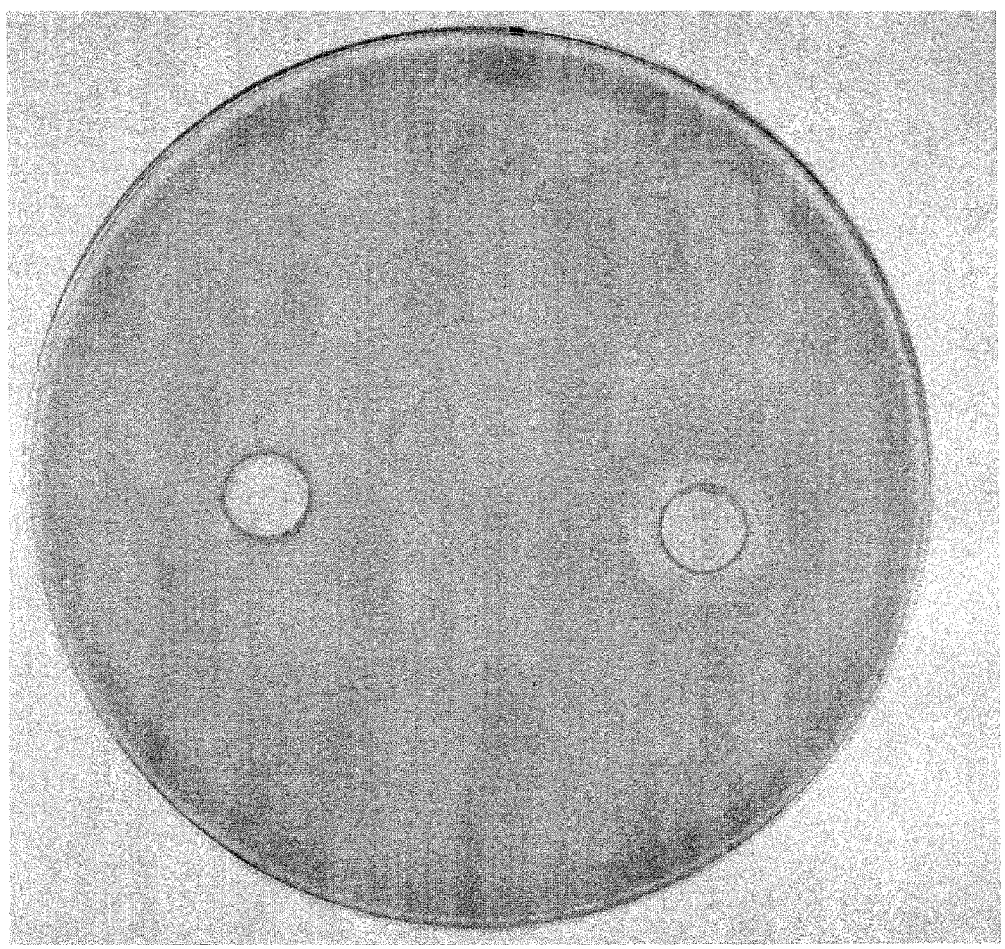
FIG. 7 is a photograph showing a result of an inhibition zone formation test of *Staphylococcus aureus*.

As shown in FIG. 7, with the suspension including an *S. aureus* colony isolated from the skin of an AD patient, a multilayer agar medium was made using standard agar medium, and a punctured agar plate was then made with penicillin cups. On the right, 50 μl of the colony suspension of *B. subtilis* from the bathwater at McFarland 1.0 standard concentration was introduced. On the left, 50 μl of the colony suspension of *B. subtilis* used in commercially available biotic pesticides at McFarland 1.0 standard concentration was introduced. Results were determined 24 h later. An inhibition zone was observed with the colony suspension on the right.

(13.2) Test No. 2: *Candida* Suppression Test (13.2.A) Competitive Inhibition Assay with *Candida*

Figure 8:
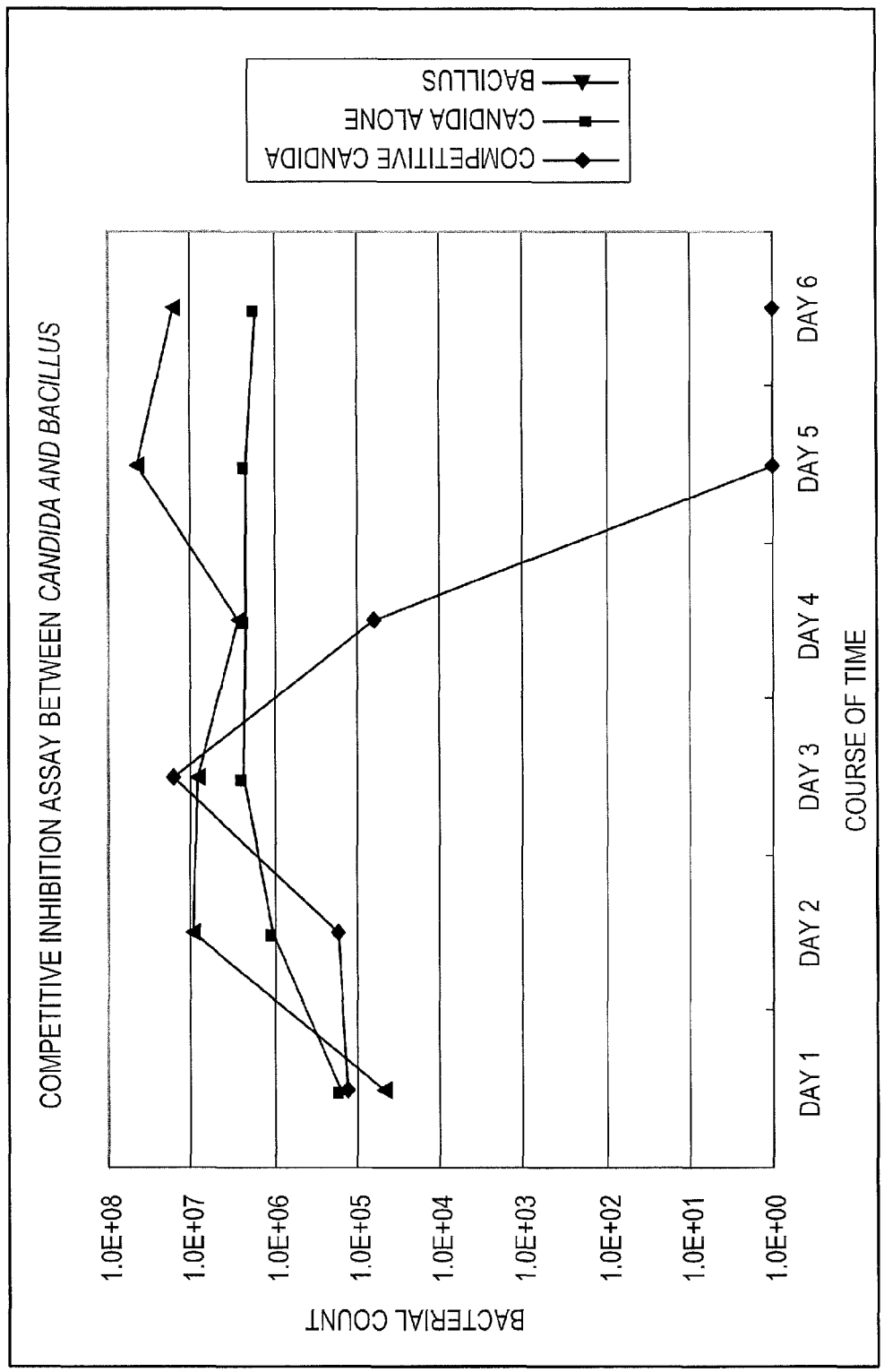
FIG. 8 is a graph showing a result of a competitive inhibition assay with *Candida*.

A *C. albicans* colony was isolated from the skin of an AD patient on a CROMagar medium and cultured for 3 days in a general broth medium. One milliliter of *C. albicans* solution ($1\times10^7$/mL) and *Bacillus* culture solution ($1\times10^7$/mL) were mixed, by 1 mL, in 200 cc of a general broth medium and spinner-cultured at 36° C. to perform a competitive inhibition assay. *C. albicans* was cultured alone as a control using the same method. *C. albicans* had completely disappeared on the $5^{th}$ day (see FIG. 8).

(13.2.B) Inhibition Zone Formation Test

Figure 9:
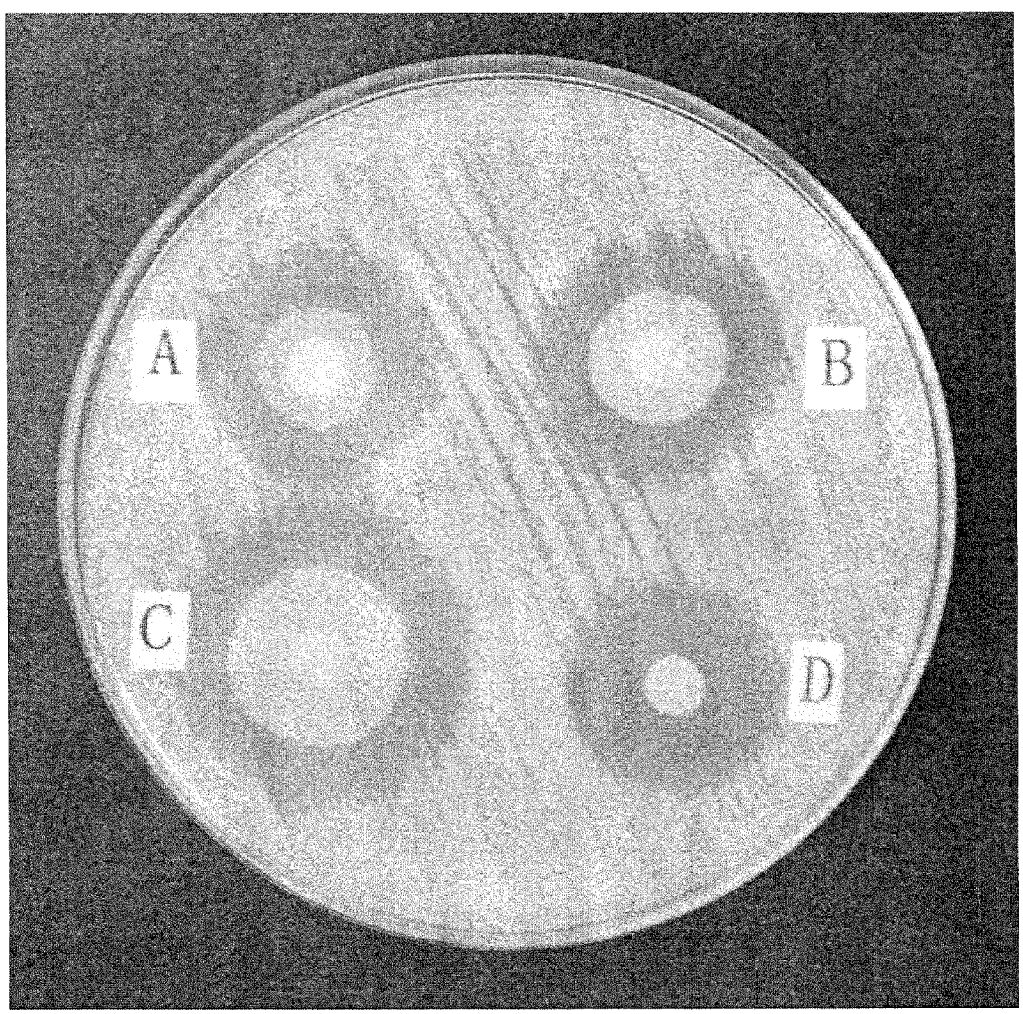
FIG. 9 is a photograph showing a result of an inhibition zone formation test of *Candida*.

As shown in FIG. 9, a *C. albicans* colony was isolated from the skin of an AD patient on a CROMagar medium, and the suspension of the colony was evenly applied to a potato dextrose agar medium using a cotton swab. A: The *B. subtilis* strain used in commercially available biotic pesticides was diluted to McFarland 0.5 standard concentration, 20 μl of which was impregnated in the disk, and cultured for 24 h at 36° C. B and C: *B. subtilis* isolated from bathwater was diluted to McFarland 0.5 standard concentration, 20 μl of which was impregnated in the disk, and cultured for 24 h at 36° C., D: As a control, 20 μl of amphotericin B at a concentration of 4 mg/mL was prepared. Results obtained are given below.

Inhibition circles of 23 mm, 24 mm, 30 mm, and 20 mm were formed for A, B, C, and D, respectively. The clear growth inhibition of *C. albicans* was observed for each type of *B. subtilis* as well as for amphotericin B.

(13.3) Test No. 3: *Malassezia* Competitive Inhibition Assay

A *Malassezia* colony was isolated from the skin of an AD patient on a CROMagar medium (see Reference 15) and *M. sympodialis* was identified with 26SrDNA-D1/D2 base sequence testing (TechnoSuruga Laboratory Co., Ltd.). *M. sympodialis* was then cultured for 3 days in Sabouraud broth medium with 2% Intrafat and allowed to grow to $10^5$ level.

Figure 10:
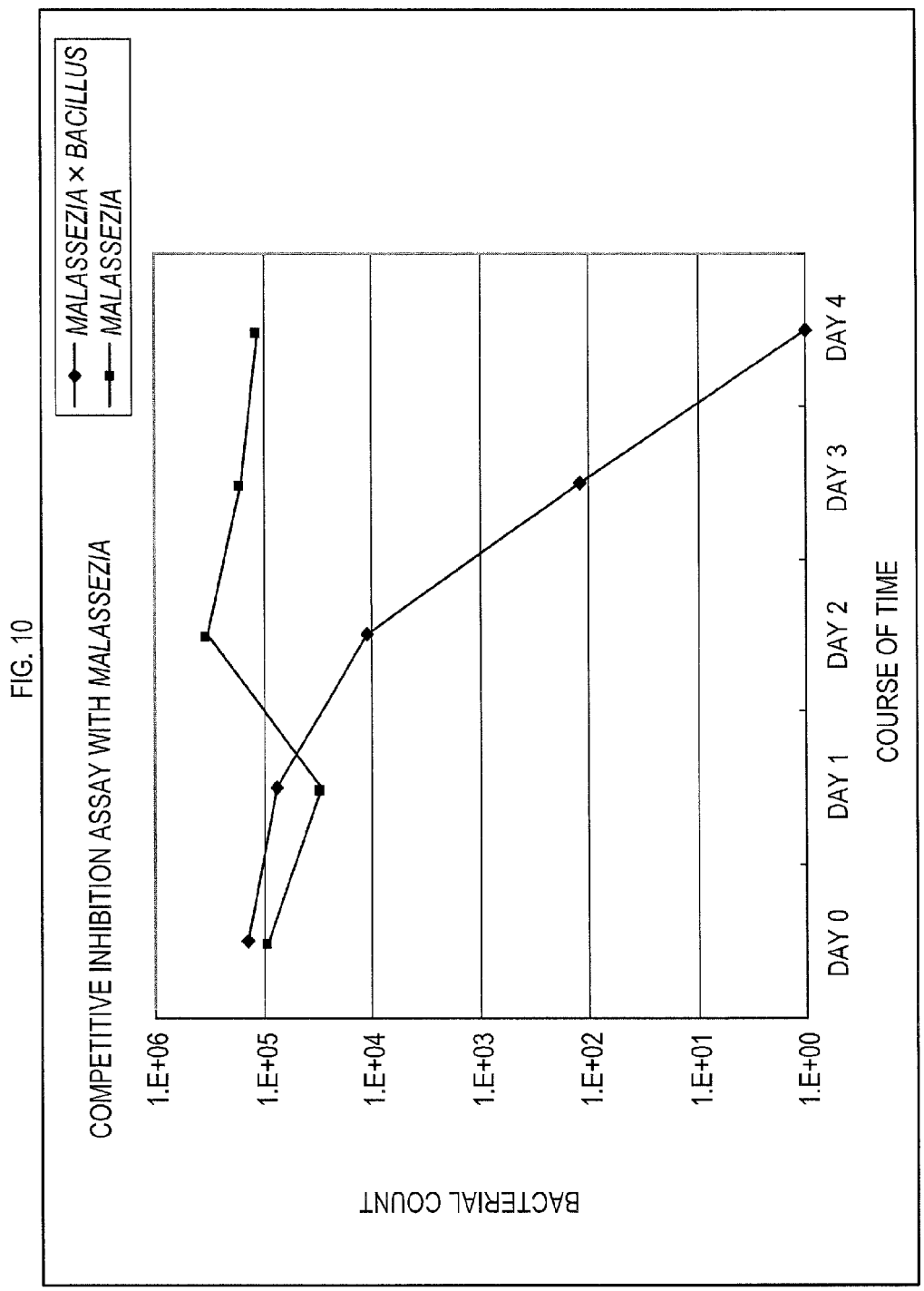
FIG. 10 is a graph showing a result of a competitive inhibition assay with *Malassezia*.

Next, 1 mL of *Bacillus* culture solution ($1\times10^7$/mL) was mixed into 150 ml of the broth medium and spinner-cultured at 32° C. to perform a competitive inhibition assay. As a control, *M. sympodialis* was cultured alone. *M. sympodialis* had completely disappeared on the $4^{th}$ day (see FIG. 10).

(14) SUPPLEMENT 2: BACTERIAL TYPES IN BST BATHWATER DURING TREATMENT (TYPICAL BATHWATER EXAMPLES ARE PRESENTED)

Bacteria in the bathwater were aerobically cultured using standard R2A medium, desoxycholate MGYM, potato dextrose, and mannitol salt agar medium with egg yolk (MSEY agar medium), and classified using the BD BBL Crystal GP. E/NF kit (see Table 4).

The dominant bacterium in the bathwater was *Bacillus*.

TABLE 4

| Case 1 (CFU/ml) | |
|---|---|
| *Bacillus circulans* | $2.2 \times 10^6$ |
| *Bacillus sphaericus* | $4.0 \times 10^5$ |
| *Bacillus subtilis* | $3.4 \times 10^5$ |
| *Paenibacillus alvei* | $2.0 \times 10^5$ |
| *Brevundimonas vesicularis* | $1.8 \times 10^3$ |
| Case 2 | |
| *Bacillus circulans* | $2.7 \times 10^8$ |
| *Bacillus subtilis* | $1.1 \times 10^7$ |
| *Bacillus megaterium* | $3.0 \times 10^6$ |
| *Bacillus cereus* | $1.0 \times 10^5$ |
| *Chromobacterium violaceum* | $3.0 \times 10^5$ |
| *Staphylococcus aureus* | $1.0 \times 10^4$ |
| *Myroides odoratus* | $2.6 \times 10^3$ |
| *Escherichia coli* | $6.0 \times 10$ |
| Case 3 | |
| *Bacillus circulans* | $2.0 \times 10^7$ |
| *Bacillus subtilis* | $2.0 \times 10^6$ |
| *Bacillus sphaericus* | $2.0 \times 10^5$ |
| *Bacillus licheniformis* | $2.0 \times 10^5$ |
| *Bacillus firmusl* | $2.0 \times 10^5$ |
| *Acinetobacter baumannii* | $9.0 \times 10^2$ |
| *Empedobacter brevis* | $7.4 \times 10^2$ |

(15) SUPPLEMENT 3: TESTING AND DISCUSSION OF THE SAFETY OF BST (15.1) Infection Testing of the Baths Used at the Inventor's Facility by an External Institution

*Legionella pneumophila* infection is a problem at hot springs and 24-h circulation type bathes.

By Sep. 10, 2013, all 159 safety tests for *Legionella* performed over 7 years by an outside testing agency on BST baths at the inventor's facility have been negative. The cooling and centrifugal concentration method (BML Co., Ltd.) was used for *Legionella* testing.

*S. aureus* of ≥1 CFU/mL was detected in 11 of the 166 tests (6.6%).

*Colibacillus detection* was positive in 73 of the 153 tests (47.7%), 65% of which was found 1-10 CFU/mL.

After such detections, bathing was suspended, and none of the above bacteria were detected again on the following day.

(15.2) *Legionella pneumophila* Survival Assay (15.2.A) Competitive Inhibition Assay with *Legionella Pneumophila*

ATCC33152 *L. pneumophila* was cultured in BCYE alpha broth, with 3 mL of $1.0 \times 10^7$ CFU/mL mixed into 150 mL of BCYE alpha broth. Then, 1 mL of *Bacillus* culture solution ($1.2 \times 10^6$/mL) was added, and spinner-cultured at 36° C. to perform a competitive inhibition assay.

As a control, *L. pneumophila* was cultured alone. The numbers of bacteria were measured on BCYE alpha, WYO alpha, and GVPC alpha agars.

Figure 11:
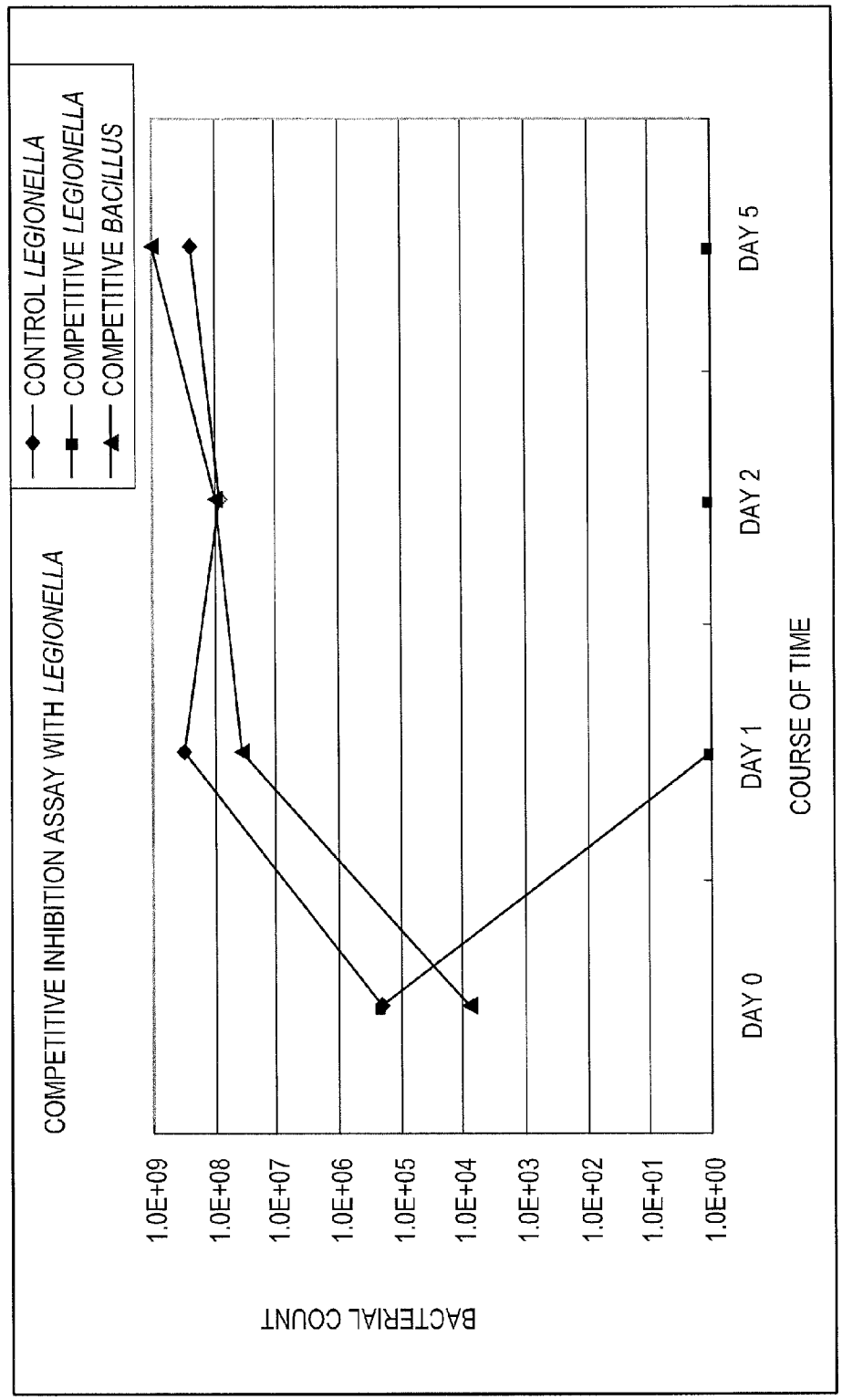
FIG. 11 is a graph showing a result of a competitive inhibition assay with *Legionella*.

*Bacillus* proliferation was extremely strong, and no *Legionella* colonies were noted on the following day (see FIG. 11).

(15.2.B) Input Test into *Bacillus* Culture Solution and LAMP Assay

A bath filled with 10 L of *Bacillus* culture solution and a bath filled with 10 L of tap water were aerated at 35° C. for 7 days. Next, *L. pneumophila* ($5.0 \times 10^7$) was added, and the bacteria were observed by the LAMP (Loop-mediated Isothermal Amplification). The sensitivity was CSF/100 mL.

TABLE 5

| | 3rd day | 7th day | 14th day |
|---|---|---|---|
| *Bacillus* + *Legionella* | − | − | − |
| Normal water + *Legionella* | + | + | + |

*Legionella pneumophila* was no longer detected on or after the $3^{rd}$ day in the bath containing *Bacillus* culture solution.

(15.2.C) Inhibition by the Bathwater Itself

Two flasks were each charged with 200 cc of BST bathwater. In 1 flask, hot air sterilization for 30 min at 121° C. was performed twice at 12-h intervals, and *Bacillus* was confirmed as negative in an agar medium. Then, *L. pneumophila* ($4.2 \times 10^6$) was added to each of the 2 flasks. After spinner culture for 6 days at 36° C., the LAMP results for both the flasks were found to be negative.

In general, it is said that *Legionella* generation time is 4-6 h, while *Bacillus* generation time is 40-50 min. Thus, reproductive capability differs greatly between these 2 bacterial types.

Test results also showed that in BST, L, *pneumophila* reproduction is inhibited by competitive inhibition by *Bacillus* and by the fatty acid etc., which is a growth inhibitory factor of *Legionella*, present in the bathwater.

(15.3) Discussion of Other Microbes that could Cause Infection (15.3.1) Protozoans The bathwater is not changed for long periods in BST. Therefore, protozoans can arise and scum may appear. When this happens, *Trinema* and *Amoeba* can be observed using a microscope by the same method as that used for the long-term exposure method of general sewer wastewater processing.

*Entamoeba hystorica* survives for 3 days at 30° C. and loses life activity in 5 min at 50° C. (see Reference 17).

Therefore, this should not be a problem at the typical bath temperature used in Japan, which is between 38° C. and 40° C.

*Cryptosporidium parvum* is a pathogenic protozoan that causes problematic water-borne infectious disease. However, mosquito oocysts that contain these protozoa become inactive after 45 days at 30° C., 15 days at 40° C., and around 7 days at 45° C. (see Reference 16). Therefore, infection should not be a problem at normal bath temperatures. *Giardia lamblia* loses life activity in 1 day at 37° C. and in 5 min at 55° C. (see Reference 17).

(15.3.2) Viruses

Many pathogenic viruses are unlikely to cause an infection through bathwater. However, in Japanese households, multiple people may bathe in the same BST bathwater. Heat-resistant viruses, Norovirus and Rotavirus in particular, could cause infections through bathwater. BST should be temporarily discontinued if gastrointestinal infection symptoms are present.

(15.4) BST Safety Testing (Toxicity Assay)

(15.4.1) Acute Toxicity Assay Using Medaka Fish

Bathwater (at the same concentration as the *Bacillus* culture solution) was poured into 10 L baths at 0, 20, 40, 60, 80, and 100% concentrations after a patient had bathed in it for 20 days. Ten medaka fish were placed in each bath and aeration was provided. An exposure assay was performed for 96 h, with an oxygen concentration of 65-72%, a pH of 8.2-8.7, and a water temperature of 25° C. As only 1 medaka fish died, the results indicated that there was no toxicity for medaka fish.

TABLE 6

| Course of Time | After 24 h | After 48 h | After 72 h | After 96 h |
|---|---|---|---|---|
| 100% | 10 | 10 | 10 | 10 |
| 80% | 10 | 10 | 10 | 10 |
| 60% | 10 | 10 | 10 | 10 |
| 40% | 10 | 9 | 9 | 9 |
| 20% | 10 | 10 | 10 | 10 |
| 0% | 10 | 10 | 10 | 10 |

(15.4.2) Human Oral Administration Assay

Twenty-six volunteers [13 of whom (50%) had higher than normal IgE and allergic symptoms of some type] drank 45 cc/day of the *Bacillus* culture solution of the same concentration as the bathwater for 6 days. Changes in symptoms were observed, and 30 items for blood biochemistry, urine analysis, and occult blood testing were collected before and after oral administration. No abnormal blood, biochemistry, or urine scores were observed.

There were no changes in the items of IgE (RIST) measurements, CRP assays, A/G ratios, or the $\alpha 2$, $\gamma glb$, white blood cell (WBC) count, or eosinophil levels, which are the indicators of allergy and inflammation, in particular. Occult blood tests were positive for 2 subjects (7.7%), but no symptoms such as diarrhea were observed in these subjects; a subsequent colonoscopy revealed no abnormalities.

Soft stools in 4 subjects were noted as subjective symptoms, 2 of whom exhibited temporary diarrhea. One subject exhibited mild facial rubefaction and 1 subject exhibited throat discomfort. Therefore, changes were noted in 6 subjects (23%). The subject with mild facial rubefaction continued to experience this symptom throughout the course of administration. All subjects who experienced such symptoms were able to continue with oral administration, and these symptoms disappeared quickly after completing the oral administration course.

In the administered culture solution, $1.4 \times 10^7$ CFU/mL of *B. subtilis* and $2 \times 10^7$ of *B. circulars*, etc., were observed.

[Testing Items]

IgE (RIST), glucose, TP, UA, UN, CREA, TCHO, LDL, TG, AST, ALT, LDH, ALP, γ-GTP, ZTT, ChE, AMY, IgE (RIST), CRP assay/Fractionation of protein (A/G ratio, albumin, α1, α2, β, and γ) WBC, RBC, Hb, Ht, blood platelet count, differential WBC count (Baso, Eosino, Stab, Seg, Lympho, Mono, Neutr)

Fecal Occult Blood/OC—HEMO

Urine analysis, qualitative (sugars, specific gravity, occult blood reaction, protein reaction, pH, qualitative test of urobilinogen, bilirubin Qualitative test of WBCs, nitrite/qualitative, and qualitative test of ketone)

(16) CLINICAL COURSE OF CHANGE IN NUMBER OF *STAPHYLOCOCCUS AUREUS* ON AD PATIENT'S SKIN IN BST

Change in the number of *Staphylococcus aureus* colonies on an AD patient's skin one month after initiation of BST was measured using a stamp medium (mannitol salt agar medium with egg yolk, Atect. Co., Ltd.).

Using the stamp medium (area: 25 cm$^2$), the number of *Staphylococcus aureus* colonies on the patient's skin was measured before and after BST, The colonies were collected from the same site on the skin before bathing in the morning. Purified water was sprayed on the site, the water is absorbed with gauze, and the gauze was softly pressed against the medium for three seconds. The colonies were cultured in the incubator at 36° C. for 24 hours, and the number of the colonies was counted.

When the number of the colonies was too large to count with the naked eye, the colonies were counted with a stereoscopic microscope. The upper limit was set at 300/cm$^2$, and 7500 on the entire medium.

Figure 12:
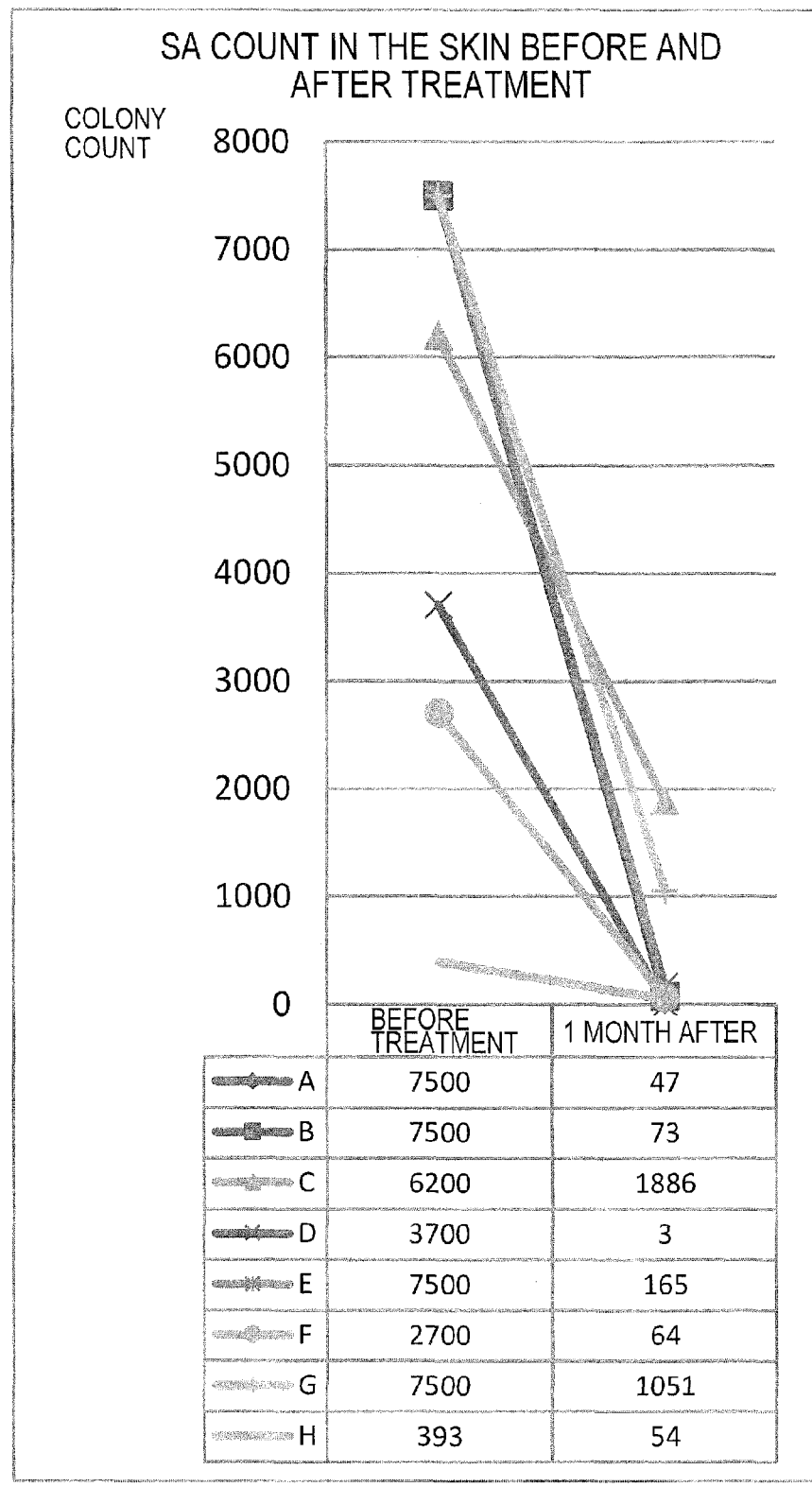
FIG. 12 is a graph showing the numbers of *Staphylococcus aureus* in the skin before and after treatment.
Figure 13:
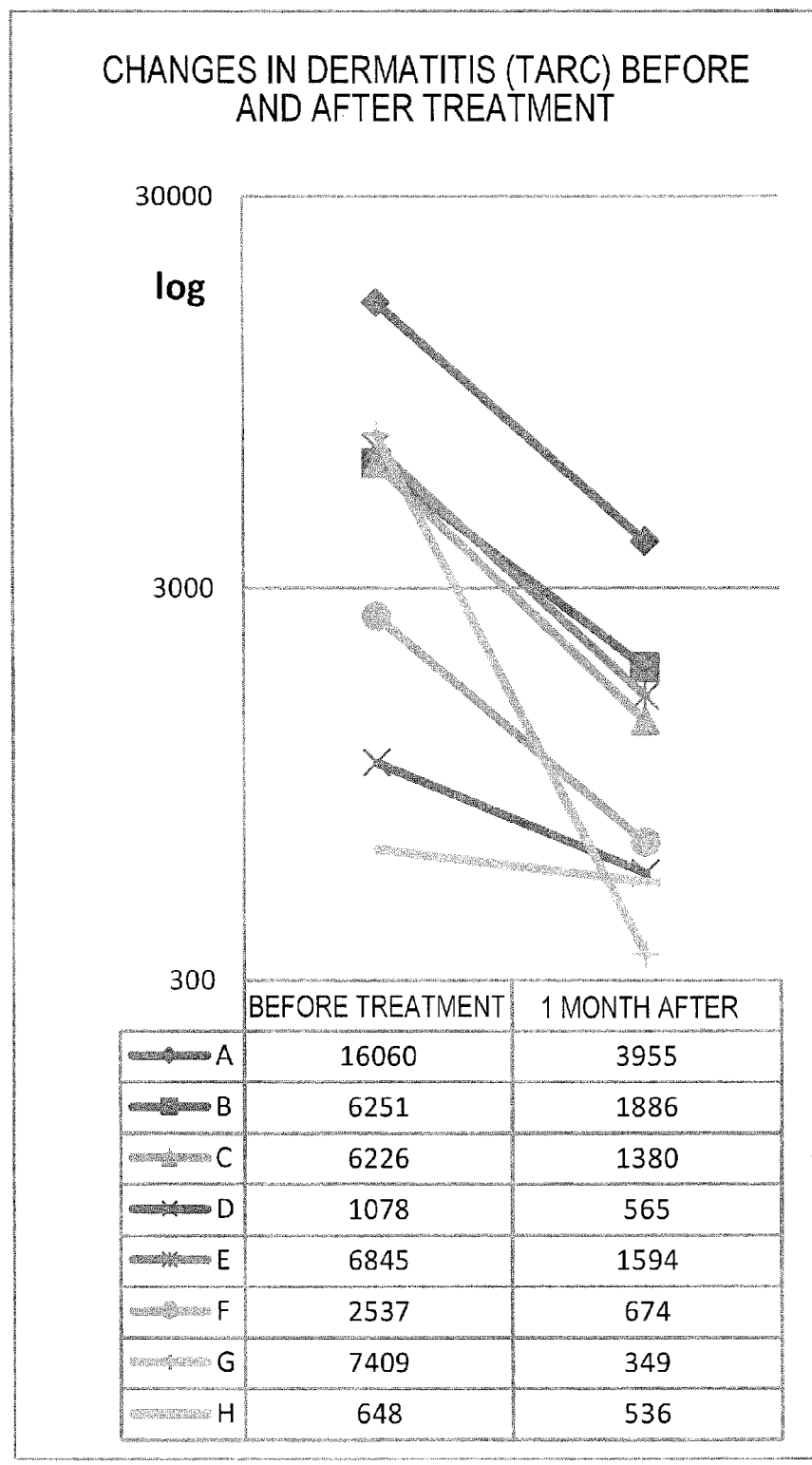
FIG. 13 is a graph showing changes in blood TARC before and after treatment.

Subjects were eight AD patients (A-H), who were hospitalized at the inventor's hospital for one month or longer some time from Oct. 10, 2013 till Apr. 30, 2014 and treated with no topical treatment but with oral administration of only biotin. Changes in the number of the colonies and blood TARC, which is an indicator of dermatitis, before initiation of BST and one month thereafter are shown in Table 7 and FIGS. 12 and 13 (normal value: ≤450).

TABLE 7

|  | A | B | C | D | E | F | G | H |
|---|---|---|---|---|---|---|---|---|
| Colony counts before treatment | ≥7500 | ≥7500 | 6200 | 3700 | ≥7500 | 2700 | ≥7500 | 393 |
| Colony counts after 1 month | 47 | 73 | 1886 | 3 | 165 | 64 | 1051 | 54 |
| TARC Before treatment | 16060 | 6251 | 6226 | 1078 | 6845 | 2537 | 7409 | 648 |
| TARC after 1 month | 3955 | 1886 | 1380 | 565 | 1594 | 674 | 349 | 536 |

Figure 14:
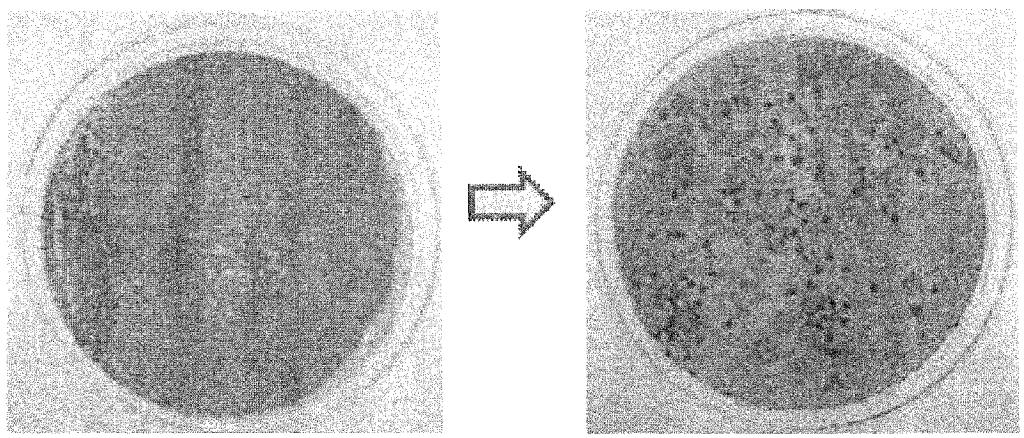
FIG. 14 is photographs showing a change in the number of colonies on a stamp medium.

The number of colonies decreased from ≥7500 to 200 per medium in one month, and white translucent *Bacillus* colonies increased instead (reference photographs are shown in FIG. 14).

These clinical study results show that *Staphylococcus aureus*, which is a complicating factor of atopic dermatitis, on the skin clearly decreased through BST for one month. It is understood that, with the decrease in *Staphylococcus aureus*, TARC, which is an indicator of dermatitis, decreased conspicuously and atopic dermatitis improved.

(17) PREFERRED CONDITIONS FOR PERFORMING BST

Preferred conditions for performing BST are described below. The method for treatment of atopic dermatitis and infectious dermatitis with biological spa therapy described herein is a method that seeks to cure or alleviate symptoms of atopic dermatitis by bathing in a bathwater containing, as dominant bacteria, not less than $10^5$ Bacillus bacteria per 1 mL of the bathwater. Cure or alleviation of symptoms of atopic dermatitis can be sought by this method.

It is necessary to culture Bacillus bacteria, which are useful bacteria, in the bathwater. In BST, it is advisable for the bathwater to contain, as dominant bacteria, not less than $10^5$ Bacillus bacteria, preferably not less than $10^7$ Bacillus bacteria, per 1 mL of the bathwater. It is assumed that an ecosystem is created in the bathwater by a lot of soil bacteria and/or protozoa. Soil bacteria are generally classified into Gram-negative proteobacteria including nitrifying bacteria, Gram-positive Actinobacteria, Gram-positive Firmicutes including Bacillus, and so on. It is dominant bacteria in the bathwater that serve an especially important function in BST.

It is important for dominant bacteria in the bathwater to meet various requirements such as: to have very low pathogenicity; to have strong inhibitory effect against pathogenic bacteria such as dermal fungus and Staphylococcus aureus and have strong inhibitory effect against pathogenic bacteria in the bathwater; to decompose and metabolize waste products discharged from the human body, whereby inhibiting chemical substances harmful to dermatitis from occurring in the bathwater; to inhibit pathogenic bacteria such as yeast and fungus in the bathwater, whereby enabling maintenance of water quality suitable for treatment; and to stimulate skin immune system to correct Th2-dominant allergic immunity. As bacteria that meet these requirements, Bacillus bacteria in the Gram-positive soil are most suitable. In BST, it is advisable for the bathwater to contain, as dominant bacteria, about $10^5$-$10^8$ Bacillus bacteria per 1 mL of the bathwater. In order for Bacillus bacteria to exist as dominant bacteria, it is preferable to appropriately perform management of temperature, oxygen, and nutrient supply.

It is preferable to contain, as Bacillus bacteria, at least one selected from a group consisting of Bacillus subtilis, Bacillus licheniformis, Bacillus sphaericus, Bacillus circulans, Bacillus megaterium, Bacillus coagulans, Bacillus firms, Bacillus aneurinolyticus, Bacillus badius, Bacillus pumilus, Bacillus thuringiensis, Bacillus clausii, Bacillus cereus, Bacillus polymyxa, Bacillus vietnami, Bacillus polyfermenticus, and Bacillus lentus.

These Bacillus bacteria have an effect of inhibiting pathogenic bacteria, as a mechanism of nature. Such bacteria and subspecies thereof can be used in the fermentation process in preparation of the bath agent and in the production process of the bath agent and culture fluid for bathing containing such useful bacteria using biotechnology, taking into consideration safety to human bodies. What bacteria or subspecies thereof are to be used is not limited in particular.

In the above-described method for treatment, it is preferable to maintain an oxygen concentration in the bathwater at 2 mg/L or more by aerating the bathwater, and it is more preferable to maintain the oxygen concentration in the bathwater at 3-5 mg/L. Especially, when one week has passed since the fermentation powder (Bacillus powder) is suspended in the bathwater, or in the acute phase of dermatitis, in which much desquamation and exudate from the skin occur, oxygen consumption by microorganisms in the bathwater is increased due to decomposition of organic substance. Thus, it is preferable to maintain the oxygen concentration at about 3-5 mg/L.

In the BST bathwater, it is preferable to decompose and metabolize waste products discharged from fermentation powder (Bacillus powder) and/or from the human body. In a case where anaerobic metabolism has been performed by obligate aerobes and/or facultative anaerobes due to decrease in oxygen concentration in the bathwater, hydrogen sulfide ($H_2S$), methane ($CH_4$), mercaptan, and a lower fatty acid such as propionic acid and N-butyric acid, which are harmful to the human body and could be a cause of foul odor, may be produced in the bathwater, and these could exacerbate dermatitis.

Therefore, it is preferable to maintain an aerobic state of the bathwater by always aerating the bathwater. In general, in order to inhibit anaerobic metabolism from occurring, it is advisable to maintain the oxygen concentration in the bathwater at 2 mg/L or more. Moreover, in order to maintain efficiency in decomposition and metabolism of waste products by sufficient oxygen supply, it is preferable to maintain the oxygen concentration at about 3-5 mg/L. If the oxygen concentration becomes greater than that level, reduction in the number of bacteria is likely to occur due to consumption of source of nutrients by bacteria. Many of useful Bacillus bacteria are obligate aerobes, and thus, it is preferable to create an aerobic environment in the bathwater so that Bacillus bacteria can exist as dominant bacteria. As for oxygen supply, the bathwater at the bottom of the bathtub, where water flow is not caused sufficiently by a mere aeration, may get into an anaerobic condition, and thus, it is preferable to agitate the bathwater thoroughly in the bathtub.

It is preferable that the temperature of the bathwater is always maintained within a range of 30-45° C. In BST, useful bacteria in the bathwater perform metabolism effectively, and inhibit pathogens while decomposing waste products. In general, an optimal temperature for growing fungus and yeast is 25-30° C., a temperature at which fungus and yeast can grow is 0-40° C., and an optimal temperature for growing common bacteria is 35-38° C. Especially, in order to inhibit growth of fungus and yeast that adversely affect atopic dermatitis, it is preferable to keep the temperature at 30° C. or higher. In order to allow useful bacteria in the bathwater to perform metabolism, to decompose waste products, and to inhibit growth of fungus and yeast with efficiency, it is preferable to maintain the temperature at 35-40° C. continuously.

Furthermore, it is also preferable that the temperature of the bathwater is raised to a range of 45-55° C. during a high-temperature treatment, and is maintained within a range of 30-45° C. except during the high-temperature treatment. Especially, in order to inhibit pathogenic bacteria including protozoa and to maintain superiority of Bacillus bacteria in the bathtub, it is effective to elevate the water temperature to 40-50° C. regularly, taking advantage of properties of Bacillus bacteria, i.e., spore formation and high heat-resistance.

[Verification of Effects of Treatment at 50° C.]

Bacteria are classified into three groups according to optimum growing temperatures; i.e., low-temperature bacteria (10-20° C.), medium-temperature bacteria (30-40° C.), and high-temperature bacteria (50-60° C.). Most pathogenic bacteria are classified into medium-temperature bacteria, whereas Bacillus bacteria, which are soil bacteria, can grow under high temperature, has spore-forming capacity, and cannot be inactivated even at 100° C. once spores are formed.

*Staphylococcus aureus, Candida, Bacillus* in the bathwater were spinner-cultured at 36° C. in a general broth medium, and after the numbers of the respective bacteria were measured, they were high-temperature-treated at 50° C. for five hours. Immediately after the high-temperature treatment, the numbers of the respective bacteria were measured. Bacteria cultured at 36° C. were used as controls. *Legionella pneumophila* was cultured in BCYE alpha broth. The results are shown in Table 8 (CFU/mL).

TABLE 8

| | Before treatment | Immediately after treatment | Control | Treatment rate |
|---|---|---|---|---|
| *Staphylococcus. aureus* | $3.4 \times 10^8$ | $4.0 \times 10$ | $1.3 \times 10^9$ | 100.0% |
| *Candida* | $4.0 \times 10^7$ | 0 | $2.2 \times 10^6$ | 100.0% |
| *Legionella* | $1.6 \times 10^7$ | $1.6 \times 10^3$ | $1.6 \times 10^7$ | 99.9% |
| *Bacillus* | $2.2 \times 10^7$ | $2.4 \times 10^7$ | $1.4 \times 10^7$ | 0.0% |

Some cases were observed in which atopic dermatitis of outpatients deteriorated. Bathwater used by such outpatients was tested and many fungi (filamentous fungi) were detected in the bathwater. The fermentation powder originally contains fungi in the fermentation process, and the patient's skin is observed to be infected with many fungi; however, fungi are inhibited from growing in the bathwater and not detected.

When the temperature of the bathwater becomes low, activity of *Bacillus* bacteria is reduced, and activity of fungi is increased instead. As a result, large growth of fungi is likely to occur in the bathwater. AD patients are often very allergic to fungi and, thus, dermatitis may deteriorate if such patients use the bathwater in which fungi are dominant bacteria. Therefore, it is important to prepare bathwater in which *Bacillus* bacteria are dominant bacteria, using some techniques.

As one of the techniques for preparing bathwater in which *Bacillus* bacteria are dominant bacteria, it is effective to continually control temperature enabling inhibition of fungal growth (35° C., and around 40° C., preferably). It is assumed that, in the folk remedy, such a temperature control was not conducted. That is, it is assumed that the temperature of the bathwater decreased to room temperature as a result of being uncontrolled after bathing, and that the bathwater was heated at the time of next bathing, which means that proper fungal control was not necessarily conducted.

The bathwater is changed when dermatitis deteriorates due to bathing or when notable improvement of dermatitis is observed. However, as a rough guide, it is preferable that the bathwater is changed when a concentration of ammonium ion in the bathwater has increased to 70 ppm or more, or when a concentration of nitric acid in the bathwater has increased to 300 ppm or more. Averagely, in the case of severe atopic dermatitis, it is preferable that the bathwater is changed after continued use thereof over one to two months.

In the bathwater, metabolite of a bath agent and/or waste products discharged from the human body is accumulated. Especially, protein component from the human body causes accumulation of nitrogen component. Examples of actual bathwater are shown in Table 9.

TABLE 9

| Course of time | $1^{st}$ day of bathing | $14^{th}$ day | $21^{st}$ day | $28^{th}$ day |
|---|---|---|---|---|
| pH | 7.6 | 7.3 | 7.1 | 7.0 |
| $NH_4^+$ (ppm) | 2.0 | 2.9 | 4.3 | 35.4 |
| $HNO_3$ (ppm) | 62 | 83 | 160 | 260 |

Accumulation of nitrogen compound causes exacerbation of atopic dermatitis, and it is known that nitrogen compound is an indicator of water quality management based on clinical experience. Rough standards are 70 ppm or more in the case of ammonium ion ($NH_4^+$), and 300 ppm or more in the case of nitric acid ($HNO_3$). In the case of severe atopic dermatitis, the above-described water quality management can be achieved by changing the bathwater in about 1-2 months. It is preferable for growth of *Bacillus* bacteria to resupply nutritional component of a bath agent, especially dietary fiber, each time the bathwater is changed.

It is preferable to mix, in the bathwater, powder or liquid containing a large amount of *Bacillus* bacteria as a bath agent. Fermented Makomo is used currently as such a bath agent. The fermented Makomo contains a large amount of useful *Bacillus* spores ($1 \times 10^8$ CFU/g or more), to thereby enable the bathwater to have a bacterial environment therein containing *Bacillus* bacteria as dominant bacteria. In addition, fermented Makomo contains dietary-fiber-based nutritious substances required for growth of bacteria in the bathwater. However, as long as the above-described conditions are met, to be the fermented Makomo in itself is not a requirement as a bath agent, and whether fermented Makomo is powder or liquid is no object.

In a case where the bath agent to be mixed into the bathwater is powder (the fermented Makomo, for example), a particle size thereof is preferably 30-100 μm in diameter in order to increase suspended particles and to inhibit deposition at the bottom of the bathtub. Such suspended particles serve as a nutrient source for bacteria as well as places to which bacteria attach for growth thereof, and thus, contribute to maintenance of the number of *Bacillus* bacteria. An important thing for a bath agent is that the component thereof does not produce an allergy, and in the case of the fermented Makomo, it is preferable that fermentation has progressed well and protein component is decomposed sufficiently. Moreover, it is preferable that harmful microorganisms are reduced during fermentation process.

Nevertheless, the spa therapy described herein is not limited to a bathing method such as using only the fermented Makomo as a bathing agent, and includes use of fermented plant containing a large amount of *Bacillus* bacteria. Such a fermented plant is obtained by fermenting a plant other than Makomo (e.g., gramineae plants such as reed, *miscanthus*, and rice straw, and materials of plant origin such as bran, fallen leaves, wood chips, and cereal).

The bathing agent containing useful *Bacillus* bacteria may be prepared without fermentation of plant-derived materials, and may be prepared by culturing a large amount of useful bacteria using solid medium or liquid medium and utilizing such bacteria in liquid form or in the form of powder prepared by drying and powdering the bacteria after spore is formed. A method utilizing such a bathing agent is also included in the therapy described herein.

Meanwhile, one of components that stabilize the water quality of the bathwater and facilitate growth of *Bacillus* bacteria is a humic substance (see Reference 19). The reason why the bathwater exhibits blackish brown is existence of humus components. The humus components are formed in the process of fermentation of plants such as Makomo. The humus components are classified into humic acid, fulvic acid, and hyumin. BST requires existence of humus components in the bathwater. Such humus components are replaced by changing the bathwater, and effects such as adsorbing harmful substances are maintained. For example, a concentration of salt (NaCl) excreted from human bodies is not increased and substantially constant in the bathwater, which is considered to be associated with effects of the humic substance adsorbing sodium ions. When the salt concentration increases, useful bacteria can no longer grow.

It is known that the humus components such as humic acid, fulvic acid, and hyumin have an antibacterial effect. When measured at the inventor's hospital, 0.6-1.0 g of humic acid is contained in 10 g of fermentation powder of Makomo. However, in the test at the inventor's hospital, antibacterial effect caused by the humic substance was not observed at the concentration thereof contained in the bathwater. In BST, it appears that the humic substance contributes to improvement of dermatitis through removal of harmful substances in the bathwater, stabilization of the water quality of the bathwater, and growth of *Bacillus* bacteria.

(18) REFERENCES

1) Williams H, Stewart A, von Mutius E, Cookson W, Anderson H R; International Study of Asthma, and Allergies in Childhood (ISAAC) Phase One and Three Study Groups, Is eczema really on the increase worldwide?, J Allergy Clin Immunol, volume 121, issue 4 Pages 947-954 e15 Apr. 2008
2) Ivette A. G. Deckers, Susannah McLean, Sanne Linssen, Monique Mommers, C. P. van Schayck, Aziz Sheikh Investigating International Time Trends in the Incidence and Prevalence of Atopic Eczema 1990?2010: A Systematic Review of Epidemiological Studies Published online 2012 Jul. 11. doi: 10.1371/journal.pone.0039803 PMCID: PMC3394782
3) Patrick M. Schlievert, Laura C. Case, Kristi L. Strandberg, Bea B. Abrams, and Donald Y. M. Leung Superantigen Profile of *Staphylococcus aureus* Isolates from Patients with Steroid-Resistant Atopic Dermatitis Clin Infect Dis. 2008 May 15; 46(10): 1562-1567
4) Helene Cawoy, Wagner Bettiol, Patrick Fickers, Marc Ongena: *Bacillus*-Based Biological Control of Planet Diseases Publisher in Teck Published online 19 Oct. 2011
5) Hideji Hiraoka, Orie Asaka, Takashi Ano Makoto Shoda: Characterization of *Bacillus subtilis* RB14, Coproducer of peptide antibiotics IturinA and Surfactin J. Gen. Appl. Microbiol, 38 653-640 1992
6) Augusto Etchegaray, Siu Mui Tsai, Luiz Alberto: Effect of a highly concentrated lipopeptide extract of *Bacillus subtilis* on fungal and bacterial cells, Arch Microbiol, 190, (2008) 611-622
7) Schmitt J, Langan S, Williams H C; European Dermato-Epidemiology Network: What are the best outcome measurements for atopic eczema? A systematic review, J Allergy Clin Immunol, 120, (2007) 1389-98
8) Tamaki K, Saeki H, et al. "Serum TARC/CCL17 Levels as a Disease Marker of Atopic Dermatitis." Japanese Journal of Dermatology 116.1 (2006): 27-39.
9) Hijnen D, De Bruin-Weller M, Oosting B, Lebre C, De Jong E, Bruijnzeel-Koomen C, Knol E: Serum *thymus* and activation-regulated chemokine (TARC) and cutaneous T cell-attracting chemokine (CTACK) levels in allergic disease: TARC and CTACK are disease-specific markers for atopic dermatitis, J Allergy Clin Immunol. 2004. February; 113(2), 334-40
10) Tamaki K, Kakinuma T, Saeki H, Horikawa T, Kataoka Y, Fujisawa T, et al. Serum levels of CCL17/TARC in various skin diseases. J Dematol 2006; 33:300-302
11) Sugimoto K, Ishikawa N, Terano T, Kitukawa Y, Kubosawa H, Ito S, Hattori T The importance of bacterial superantigens produced by *Staphylococcus aureus* in the treatment of atopic dermatitis using povidone-iodine. Dermatology. 2006; 212 Suppl 1:26-34.
12) Gueho, E; Midgley, G; Guillot The genus *Malassezia* with description of four new species Antonie van Leeuwenhoek; v: 69 i: 4 p: 337-55; 5/1996
13) Darabi K, Hostetler S G, Bechtel M A, Zirwas M (2009): The role of *Malassezia* in atopic dermatitis affecting the head and neck of adults, J Am Acad Dermatol, 2009 jam; 60, 125-36
14) Quantitative analysis of cutaneous *malassezia* in atopic dermatitis patients using real-time PCRMicrobiology and Immunology; v: 50 i: 7 p: 549-52; 2006 Sugita, Takashi; Tajima, Mami; Tsubuku, Hisae; Tsuboi, Ryoji; Nishikawa, Akemi
15) Kaneko T. Makimura K. Abe M et al. Revised culture-based system for identification of *Malassezia* species. J Clin Microbiol 45: 3737-3742, 2007
16) Tomokazu Kitamura, Hiroaki Morita Effect of Water Temperature on the Survival of *Cryptosporidium parvum* Oocysts by In vitro Excystation-Flow Cytometry Assay Environmental Engineering Research. Vol. 37, 2000 Public Works Research Institute, Ministry of Construction Japan
17) WHO (1996) Guidelines for Drinking Water Quality. 2nd ed vol 2 health criteria and other supporting information 1996
18) Jason Gans, Murray Wolinsky, John Dunbar Computational Improvements Reveal Great Bacterial Diversity and High Metal Toxicity in Soil Science 26 Aug. 2005: Vol. 309 No. 5739 pp. 1387-1390
19) C. E. J. van Rensburga, A. van Stratenb and J. Dekkerc An in vitro investigation of the antimicrobial activity of oxifulvic acid J Antimicrob Chemother 2000; 46: 853-854

What is claimed is:

1. A method of treating atopic dermatitis in a subject in need thereof, wherein the method comprises: suspending a fermentation powder comprising *Bacillus* bacteria spores in water to provide a bathwater containing not less than $10^5$ *Bacillus* bacteria per 1 ml of the bathwater;

maintaining the bathwater at a temperature between 35° C. and 42° C. and an oxygen concentration of 2 mg/mL or more for about one week to provide a cultured bathwater comprising $10^6$ to $10^7$ *Bacillus* bacteria per 1 mL;

and initiating daily bathing of the subject in the cultured bathwater after the about one week of maintaining the bathwater at the temperature between 35° C. and 42° C. and an oxygen concentration of 2 mg/mL or more, further wherein said cultured bathwater is used for bathing the subject daily without changing the cultured bathwater for at least one month; thereby treating the atopic dermatitis.

2. The method of treating atopic dermatitis according to claim 1, wherein at least one bacteria selected from a group consisting of *Bacillus subtilis, Bacillus licheniformis, Bacillus sphaericus, Bacillus circulans, Bacillus megaterium, Bacillus coagulans, Bacillus firmus, Bacillus aneurinolyticus, Bacillus badius, Bacillus pumilus, Bacillus thuringien-* sis, *Bacillus clausii, Bacillus cereus, Bacillus polymyxa, Bacillus vietnami, Bacillus polyfermenticus*, and *Bacillus lentus* is included as the *Bacillus* bacteria.

3. The method of treating atopic dermatitis according to claim 1, wherein, after the fermentation powder is suspended, or during a period when oxygen consumption in the bathwater is increased due to increase in organic substance in the bathwater in the acute phase of dermatitis, the oxygen concentration is maintained at 3 to 5 mg/L.

4. The method of treating atopic dermatitis according to claim 1, wherein the oxygen concentration is maintained also at a bottom of a bathtub by thorough agitation in the bathtub.

5. The method of treating atopic dermatitis according to claim 1, wherein a temperature of the bathwater is raised to a range of 45 to 55° C. during a high-temperature treatment to inhibit pathogenic bacteria.

6. The method of treating atopic dermatitis according to claim 1, wherein the bathwater is changed when a concentration of ammonium ion in the bathwater has increased to 70 ppm or more, or when a concentration of nitric acid in the bathwater has increased to 300 ppm or more.

7. The method of treating atopic dermatitis according to claim 6, wherein the bathwater is changed after continued use thereof over one to two months.

8. The method of treating atopic dermatitis according to claim 1, wherein the fermentation powder contains not less than $10^8$ CFU/g of useful *Bacillus* spores and suspending the powder in the water provides a bathwater comprising between $10^6$ and $10^7$ CFU/mL of cultured *Bacillus* bacteria.

9. The method of treating atopic dermatitis according to claim 8, wherein the fermentation powder has a particle size of 30 to 100 pm in diameter.

10. The method of treating atopic dermatitis according to claim 1, wherein suspending the fermentation powder comprising *Bacillus* bacteria in water provides a bathwater containing, as dominant bacteria, not less than $10^7$ *Bacillus* bacteria per 1 ml of the bathwater.

11. The method of treating atopic dermatitis according to claim 1, wherein the bathing is performed for between two and six hours per day.

12. The method of treating atopic dermatitis according to claim 1, wherein the bathwater is changed after continued use thereof over two to three months.

13. The method of treating atopic dermatitis according to claim 1, wherein treating the atopic dermatitis results in a reduction in thymus and activation-regulated chemokine (TARC) levels of 89.8% or more in the subject.

14. A method of treating atopic dermatitis in a subject in need thereof, the method comprising:
suspending a fermentation powder comprising *Bacillus* bacteria spores in water to provide a bathwater containing not less than $10^5$ *Bacillus* bacteria per 1 mL of the bathwater wherein the bathwater is used for daily baths by a single subject over a period of at least 1 month;
maintaining the bathwater for the same single subject for the period of at least 1 month, wherein maintaining the bathwater comprises maintaining the bathwater at a temperature in a first temperature range of between 35° C. and 42° C. for bathing, except during periodic increases to a temperature in a second temperature range of between 45° C. to 55° C. to inhibit pathogenic bacteria, and wherein the first temperature range is maintained for bathing for about one week to provide a cultured bathwater comprising $10^6$ to $10^7$ *Bacillus* bacteria per 1 mL; and
bathing the same single subject in the cultured bathwater daily for a period of at least one month without changing the bathwater.

* * * * *